United States Patent
El-Say et al.

(10) Patent No.: US 11,096,902 B1
(45) Date of Patent: Aug. 24, 2021

(54) TRANSDERMAL FILM FORMULATIONS AND METHODS OF USE

(71) Applicant: King Abdulaziz University, Jeddah (SA)

(72) Inventors: Khalid Mohamed El-Say, Jeddah (SA); Tarek Abdelnapy Ahmed, Jeddah (SA); Hossam Samir El-Sawy, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/314,094

(22) Filed: May 7, 2021

(51) Int. Cl.
| | |
|---|---|
| *A61K 9/70* | (2006.01) |
| *A61K 47/10* | (2017.01) |
| *A61K 47/32* | (2006.01) |
| *A61K 47/12* | (2006.01) |
| *C08J 5/18* | (2006.01) |
| *A61K 31/40* | (2006.01) |

(52) U.S. Cl.
CPC ............ *A61K 9/7015* (2013.01); *A61K 31/40* (2013.01); *A61K 47/10* (2013.01); *A61K 47/12* (2013.01); *A61K 47/32* (2013.01); *C08J 5/18* (2013.01); *C08J 2333/12* (2013.01)

(58) Field of Classification Search
None
See application file for complete search history.

(56) References Cited

U.S. PATENT DOCUMENTS

| | | |
|---|---|---|
| 2004/0028721 A1 | 2/2004 | Colombo et al. |
| 2006/0078603 A1 | 4/2006 | Nguyen |
| 2011/0136815 A1 | 6/2011 | Zerbe et al. |

OTHER PUBLICATIONS

Shaker et al. (Boosting transdermal delivery of atorvastatin calcium via o/w nanoemulsifying system: Two-step optimization, ex vivo and in vivo evaluation, International Journal of Pharmaceutics 578 (2020)). (Year: 2020).*
Ammar et al., "Rapid pain relief using transdermal film forming polymeric solution of ketorolac", Pharmaceutical Development and Technology, vol. 18, 2013, issue 5.
Castaneda et al., "Design and evaluation of a transdermal patch with atorvastatin", Farmacia, 2017, vol. 65, 6.
Prashar et al., "Formulation and evaluation of transdermal drug delivery system of Simvastatin using natural and synthetic permeation enhancers", Materials Science, 2014.

* cited by examiner

*Primary Examiner* — Melissa S Mercier
(74) *Attorney, Agent, or Firm* — W&C IP

(57) ABSTRACT

A transdermal film composition including a film forming polymer comprising poly(ethyl acrylate-co-methyl methacrylate-co-trimethylammonioethyl methacrylate chloride) 1:2:0.2, oleic acid, polyethylene glycol, and atorvastatin calcium. Methods of making the composition and administering the composition to deliver atorvastatin to a subject are also provided.

11 Claims, 9 Drawing Sheets

TRANSDERMAL FILM FORMULATIONS AND METHODS OF USE

FIELD OF THE INVENTION

The invention is generally related to transdermal films loaded with an antihyperlipidemic drug and methods of use thereof.

BACKGROUND OF THE INVENTION

Atorvastatin calcium (ATC) is renowned for competently and competitively inhibiting the 3-hydroxy-3-methylglutaryl-coenzyme A (HMG-CoA) reductase enzyme, and induces HMG-CoA conversion into mevalonate, therefore, interposing the cholesterogenesis pathway within the liver. ATC also reduces the low-density lipoproteins (LDL) level by elevating LDL re-uptake and deprivation [1]. A modest increase in high-density lipoproteins (HDL) and apolipoprotein A1 (apo A-I) is also evidenced to be mediated by ATC through inhibiting the cholesteryl ester transfer protein (CETP) action [2]. Consequently, ATC has been revealed to help in the prevention of coronary atherosclerosis progression by attenuating the plaque lipid-core. Besides the anti-dyslipidemic activity of ATC, it is also utilized and studied for the remediation approach of Alzheimer's disease, benign prostatic hyperplasia, and osteoporosis [3]. According to the Biopharmaceutics Classification System (BCS), ATC is a BCS class II drug-moiety, which indicates that ATC is highly permeable but exhibits poor water solubility characteristic with log P of 5.39. Subsequently, it has a low oral bioavailability only circa 14%, which is mostly due to elevated pre-systemic gastrointestinal clearance, first-pass metabolism, and inadequate intestinal absorption [4]. Besides, many gastrointestinal disturbances such as decreased appetite, diarrhea, and constipation may be experienced by patients who used oral ATC medication. Furthermore, the concomitant intake of food can potentially reduce both systemic availability and maximum drug concentration ($C_{max}$) by 25 and 9%, respectively [5]. Moreover, and owing to the excessive hepatic metabolism of oral ATC, further oxidative stress is exerted on the liver, which increases the risk of liver impairments.

Consequently, other effective alternate routes of administration should be investigated to decrease or minimize the metabolic stress that can be exerted on the liver from oral administration [6]. Transdermal drug delivery has many beneficial returns over other conventional delivery systems. As a non-invasive alternate to parenteral dosage forms, the transdermal route can avoid injection-invasiveness-related problems and issues like needle phobia [7]. Besides, the ease of access and availability of the skin with a large surface area permits many options for the placement of transdermal films on the skin [8]. Moreover, the risk of toxic side effects is minimized from transdermal films, owing to the pharmacokinetic profiles of drugs, which will be more uniform with fewer peaks, besides avoiding pre-systemic metabolism, hence improving bioavailability [9-11]. Furthermore, the ease of application and convenience is one of the greatest benefits of transdermal delivery, which leads to higher patient compliance as a result of the reduced frequencies of dosing. It is also appropriate for unconscious or vomiting patients, or those who cannot depend on self-administration [12].

The permeation through the stratum corneum (SC) is the main challenge facing the transdermal delivery of drugs, which acts as a natural defensive barrier in front of any external foreign chemicals and environmental elements [13]. The efficient amendment of this barrier with a reversible means is required to resolve such limitation. Due to the bioavailability problems with oral delivery of ATC, alternative and effective formulations for ATC delivery are needed.

SUMMARY OF THE INVENTION

The disclosure provides a combination of film-forming polymers, penetration enhancers, and plasticizers, that can be prepared utilizing a simple fabrication scheme, that provide a transdermal delivery system with enhanced efficacy and bioavailability.

An aspect of the disclosure provides a transdermal film composition, comprising a film forming polymer comprising poly(ethyl acrylate-co-methyl methacrylate-co-trimethyl-ammonioethyl methacrylate chloride) 1:2:0.2, oleic acid, polyethylene glycol (PEG), and atorvastatin calcium. In some embodiments, the film forming polymer is present at a concentration of 3-10 wt %. In some embodiments, the oleic acid is present at a concentration of 10-20 wt %. In some embodiments, the PEG is PEG 400 and is present at a concentration of 25-40 wt %. In some embodiments, the atorvastatin calcium is present in an amount of 150-250 mg. In some embodiments, the film has a thickness of 0.75-0.85 mm.

Another aspect of the disclosure provides a method of making a composition as described herein, comprising dissolving the film forming polymer in a solvent; dispersing atorvastatin calcium in the film forming polymer solution; dispersing oleic acid and PEG 400 in the film forming polymer solution; drying the solution to form a film. In some embodiments, the solvent comprises a 1:1 v/v mixture of DCM and methanol. In some embodiments, the method further comprises attaching a backing membrane to the film.

Another aspect of the disclosure provides a method of delivering atorvastatin to a subject in need thereof, comprising applying a transdermal film composition as described herein to a skin surface of the subject.

DETAILED DESCRIPTION

Figure 1:
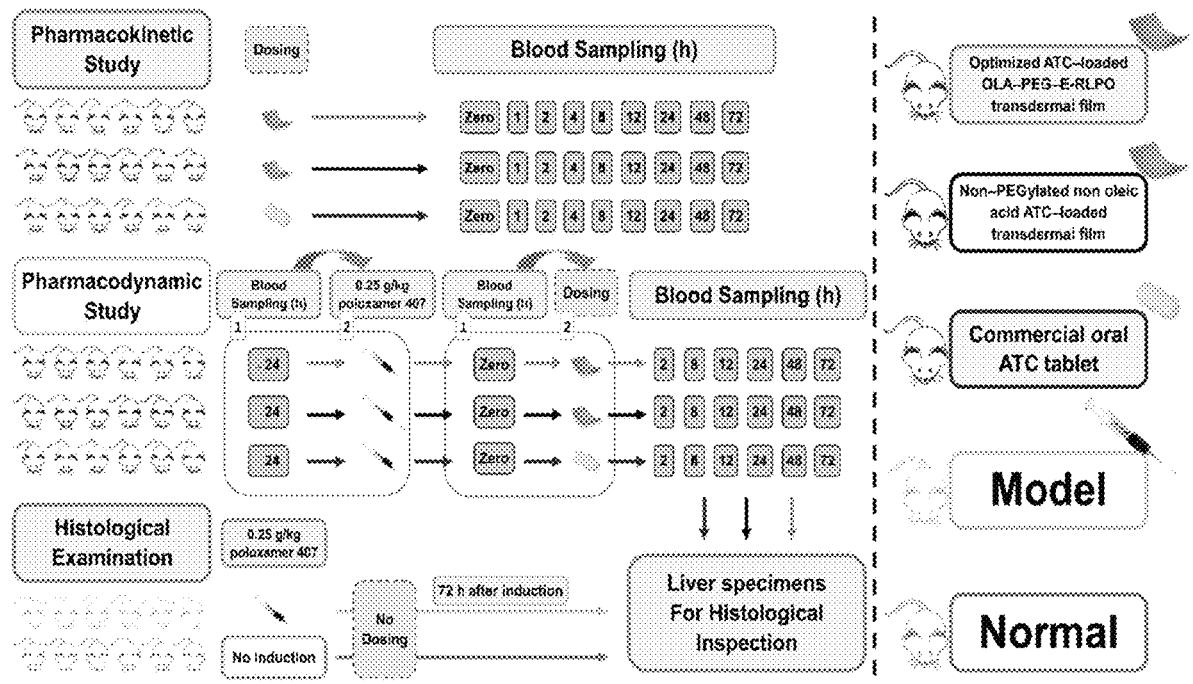
FIG. 1. Schematic illustration of the carried out pharmacokinetic, pharmacodynamic, and histopathological studies.
Figure 2A:
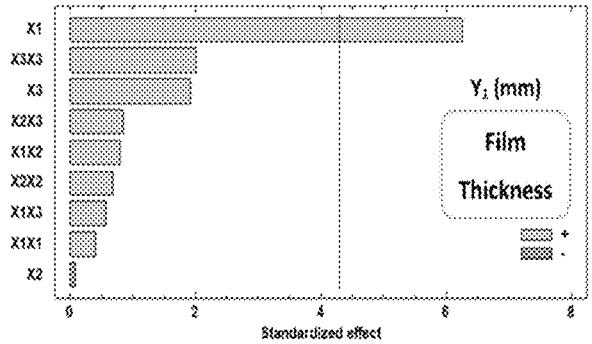
FIGS. 2A-F. Standardized Pareto charts for factors' effects on the measured responses (A) $Y_1$, (B) $Y_2$, (C) $Y_3$, (D) $Y_4$, (E) $Y_5$, and (F) $Y_6$.
Figure 2B:
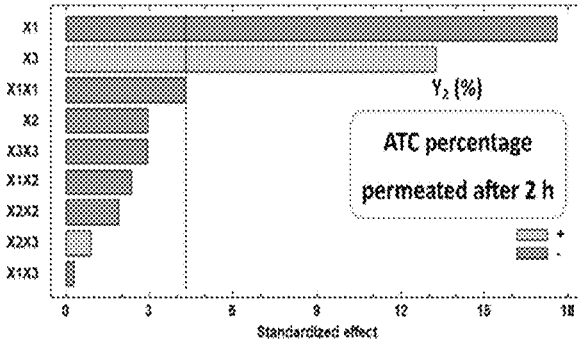
Figure 2C:
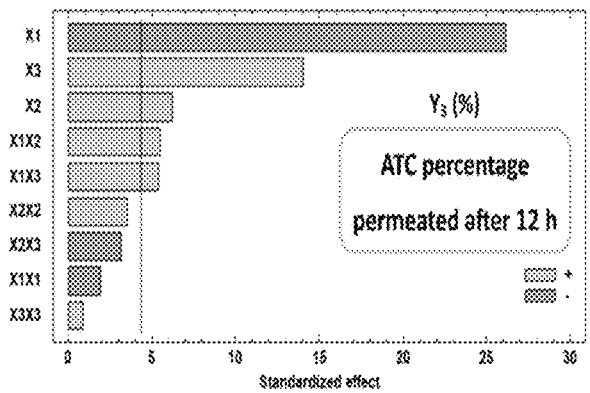
Figure 2D:
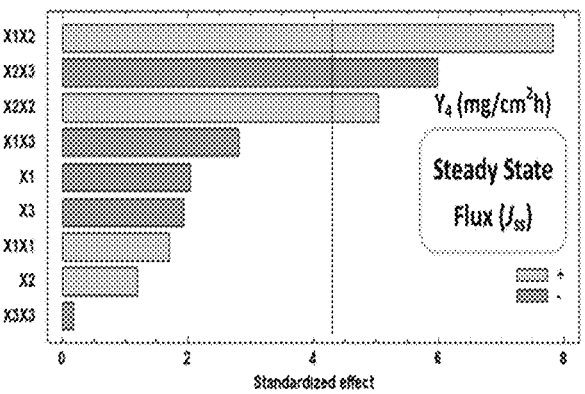
Figure 2E:
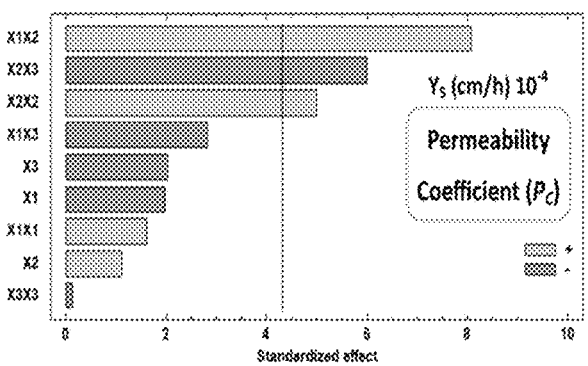
Figure 2F:
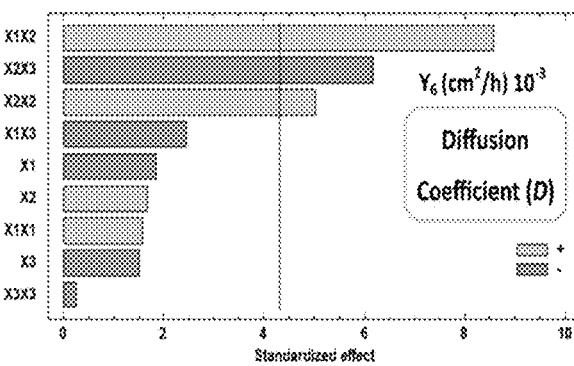
Figure 3A:
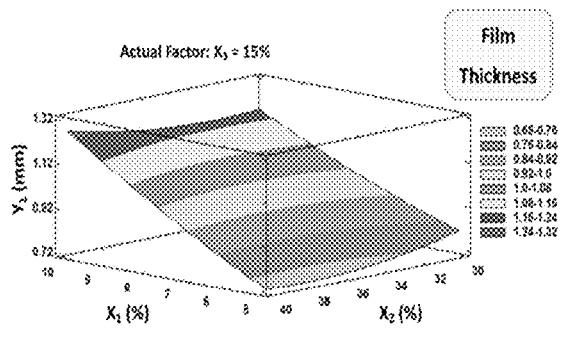
FIGS. 3A-F. Contour response surface graphs for factors' effects on measured responses (A) $Y_1$, (B) $Y_2$, (C) $Y_3$, (D) $Y_4$, (E) $Y_5$, and (F) $Y_6$.
Figure 3B:
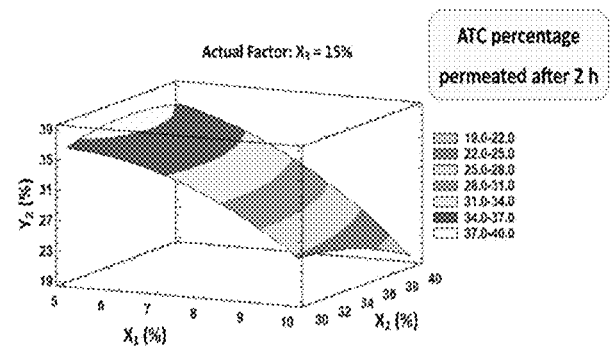
Figure 3C:
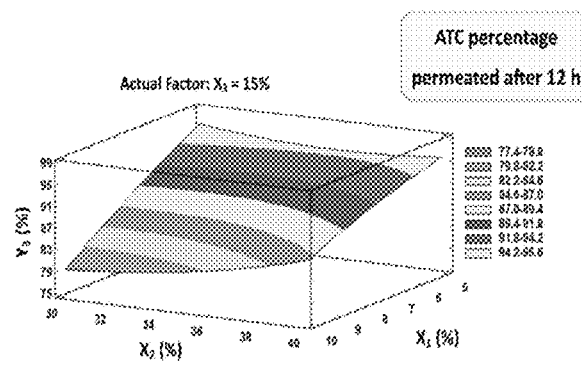
Figure 3D:
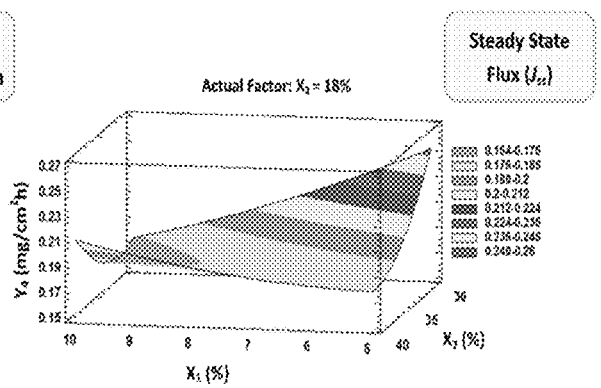
Figure 3E:
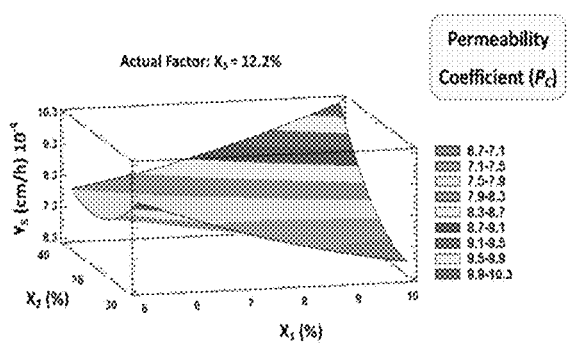
Figure 3F:
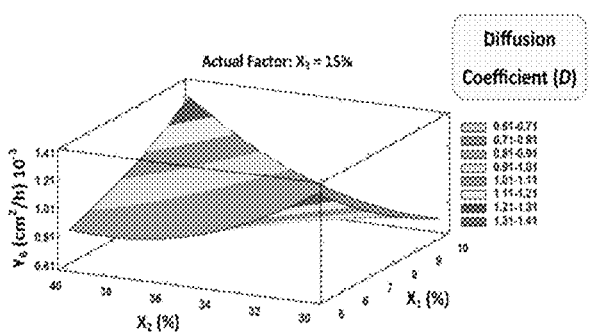

Embodiments of the disclosure provide transdermal film formulations having enhanced bioavailability of the loaded drug. The formulations include combinations of film forming polymers, penetration enhancers, and plasticizers.

A transdermal film, which may be incorporated into a patch, is a medicated film that is placed on the skin to deliver a specific dose of medication through the skin and into the bloodstream. An advantage of a transdermal drug delivery route over other types of medication delivery such as oral, topical, intravenous, intramuscular, etc. is that the film provides a controlled release of the medication into the patient, usually through either a porous membrane covering a reservoir of medication or through body heat melting thin layers of medication embedded in the adhesive. Typical components of a patch include a liner which protects the patch during storage and is removed prior to use, drug, adhesive, membrane, backing, permeation enhancers, stabilizers, preservatives, etc. In some embodiments, the film has a thickness of 0.75-0.85 mm.

In some embodiments, the film forming polymers incorporated in a transdermal film as described herein are Eudragit® synthetic polyacrylates. Eudragit® polymers are synthetic cationic, anionic and non-ionic polymers of dimethyl-aminoethyl methacrylates, methacrylic acid and methacrylic acid esters in varying ratios. Suitable Eudragit® polymers include Eudragit® RLPO (poly(ethyl acrylate-co-methyl methacrylate-co-trimethylammonioethyl methacrylate chloride) 1:2:0.2), Eudragit® RSPO, Eudragit® L100, Eudragit® NE40D, Eudragit® RL30D, Eudragit® RS30D, Eudragit® EPO, etc. In some embodiments, the film forming polymer is present at a concentration of 3-10 wt %. e.g. 4-8 wt %, e.g. about 5 wt %.

Permeation enhancers are molecules that interact with the constituents of the skin's outermost and rate limiting layer stratum corneum (SC), and increase its permeability. In a preferred embodiment, the formulation of the disclosure utilizes oleic acid (OLA) as a permeation enhancer. OLA is a fatty acid that occurs naturally in various animal and vegetable fats and oils. In chemical terms, OLA is classified as a monounsaturated omega-9 fatty acid, abbreviated with a lipid number of 18:1 cis-9. It has the formula $CH_3(CH_2)_7CH=CH(CH_2)_7COOH$. OLA mainly modifies the extracellular lipid domain of the SC, which decreases the permeation resistance of the skin via intermingling with the lipid milieu of SC. In some embodiments, the oleic acid is present at a concentration of 10-20 wt %, e.g. 17-19 wt %, e.g. about 18 wt %.

Additional skin penetration enhancers which may be incorporated into the transdermal film include, but are not limited to, sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG), surfactants and terpenes (e.g. citral).

The plasticizer preserves elasticity and drug stability, avoids films' cracking, and enhances drug permeation. In a preferred embodiment, the formulation of the disclosure utilizes polyethylene glycol (PEG) as a plasticizer. PEGs are prepared by polymerization of ethylene oxide and are commercially available over a wide range of molecular weights from 300 g/mol to 10,000,000 g/mol, each of which is compatible with the present disclosure. In a preferred embodiment, the PEG is PEG 400. In some embodiments, the PEG is present at a concentration of 25-40 wt %, e.g. 28-32 wt %, e.g. about 30 wt %.

The formulations described herein are useful for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is a statin, such as atorvastatin, fluvastatin, lovastatin, pitavastatin, pravastatin, rosuvastatin, and simvastatin. In some embodiments, the amount of active agent incorporated into the composition is 150-250 mg, e.g. 175-225 mg, e.g. about 200 mg.

The compositions of the present disclosure may also contain other components such as, but not limited to, additives, adjuvants, buffers, tonicity agents, bioadhesive polymers, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, compositions of the present disclosure further comprise one or more bioadhesive polymers. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, COOH), the presence and strength of anionic charges, sufficient elasticity for the polymeric chains to interpenetrate the mucous layer, and high molecular weight.

In an embodiment, a composition of the present disclosure includes at least one bioadhesive polymer. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments to the eye (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure also provide methods of preparing transdermal films. In an embodiments, the film forming polymer is dispersed in a solvent, e.g. water, dichloromethane (DCM), methanol, etc. In some embodiments, the solvent is a mixture of DCM and methanol, e.g. a 2:1 to 1:2 mixture, e.g. a 1:1 mixture. The drug active agent, skin permeation enhancers, plasticizers, and other additives may then be added to the solution. The preparation may then be poured onto a contained surface, e.g. a petri dish, to allow for complete evaporation of water and formation of the film. In some embodiments, the method further comprises attaching a backing membrane to the film. The film may be incorporated into known transdermal delivery devices, e.g. in a patch containing an adhesive for application to the skin.

The present disclosure also provides a method of delivering an active agent by topically administering a transdermal film as described herein. Further embodiments provide a method of treatment of a human or non-human animal subject by delivery of an active agent as hereinbefore defined. Further embodiments provide a method of enhancing the bioavailability of the active agent by topically applying a transdermal film formulation as described herein to the skin of the subject.

The compositions and dosage forms of the disclosure may be useful for the treatment of any disease or disorder that the included active agent is useful for treating. For example, if atorvastatin is used, the composition or dosage form may be useful for the treatment of high cholesterol and triglyceride levels.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. atorvastatin) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In an embodiment, the composition or dosage form of the disclosure is applied topically to any body surface, including the skin and all other epithelial or serosal surfaces. However, whilst the beneficial effects of the disclosure are particularly apparent in transdermal delivery, the utility of the disclosure is not limited and the formulations according to the invention may also be administered parenterally or enterally, eg. as implants or by intravenous, intramuscular or subcutaneous injection, by infusion, or orally.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

SUMMARY

Due to the poor bioavailability and extensive liver metabolism of atorvastatin calcium (ATC), we developed oleic acid-reinforced PEGylated polymethacrylate (OLA-PEG-E-RLPO) transdermal films of ATC as a convenient and alternative delivery system with improved bioavailability. The effect of varying levels of Eudragit RLPO, PEG 400, and oleic acid on the target product profile was optimized using the quality by design concept. The optimized ATC-loaded OLA-PEG-E-RLPO transdermal film was predicted, elaborated, and further investigated via pharmacokinetic/pharmacodynamic assessment on poloxamer-induced dyslipidemic rats. The optimized film revealed a thickness of 0.79 mm, amount of ATC permeated after 2 and 12 h of 37.34% and 97.23%, respectively with 0.172 mg/cm² h steady-state flux, $7.01 \times 10^{-4}$ cm/h permeability coefficient, and $0.713 \times 10^{-3}$ cm²/h diffusion coefficient. Interestingly, the $AUC_{0-\infty}$ of the optimized film pre-treated group was 8.6 and 2.8 folds more than those of the non-PEGylated non-oleic acid film model and the oral marketed tablet groups, respectively. The lipid profile of the optimized film pre-treated group reached normal levels after 12 h, along with the significant enhancement over the non-PEGylated non-oleic acid film and the oral marketed tablet groups. The histopathological findings revealed near-normal hepatocytes' structure of the optimized film pre-treated group. To conclude, the optimized ATC-loaded OLA-PEG-E-RLPO transdermal films maximized the antidyslipidemic activity and bioavailability of ATC via a feasible and economic approach, simultaneously. Such an approach is useful for economical industrialized scale production over other advanced drug delivery systems.

Materials and Methods

Materials

Atorvastatin calcium (ATC) was supplied as a gift from SPIMACO (Riyadh, Saudi Arabia), while Evonik Industries AG-Werk Rohm (Darmstadt, Germany) provided the Eudragit RLPO. Dichloromethane (DCM) was purchased from Prolabo (Paris, France). Acetonitrile HPLC grade and phosphoric acid were provided from Merk (Darmstadt, Germany) Oleic acid (OLA), Polyethylene glycol 400 (PEG 400), methanol, and any other compounds required for this research work were obtained from Sigma-Aldrich (St. Louis, USA). All provided chemicals and reagents were of analytical grade.

Chromatographic Conditions

In this research work, any samples containing ATC from formulations, and the ATC plasma concentrations as well, were determined using an isocratic HPLC chromatographic condition with modification [23]. The HPLC instrument was adapted with an adaptable wavelength ultraviolet-spectroscopic detector adjusted at 240 nm along with a quaternary pump, autosampler, vacuum degasser, and Winchrom software. The chromatographic separation was performed on a Phenomenex, Hypersil C18 5u column (Phenomenex, Torrance, Calif.) at room temperature. The acetonitrile: 0.1% phosphoric acid ratio at 66:34 v/v was used as a mobile phase that was pumped at a flow rate of 1.2 ml/min. For ATC extraction from the plasma samples, 1 ml of acetonitrile was added to 1 ml aliquot of a sample, exposed to 1 min vigorous shaking via a vortex, and then allowed to undergo 10 min centrifugation at 5000 rpm. The separation of the organic solvent was undertaken through evaporation at 50° C. under a nitrogen stream until complete dryness. The residue was reconstituted in 80 µl of the mobile phase and a volume of 20 µl was injected. An internal standard (IS) solution was prepared by dissolving a specified amount of simvastatin in a known volume of the mobile phase to prepare a 100 ng/ml solution. Two milliliters of the IS were applied to 500 ml of the supernatant which is furtherly extracted with diethyl ether and potassium hydroxide solution. The supernatant was evaporated under nitrogen and the residue was constituted with 200 ml of the mobile phase. The chromatographic condition utilized in this research work was in-house validated and considered sensitive, precise, robust, accurate, and selective. The limits of ATC detections and quantitation were 0.5 and 2 ng/ml, respectively.

Experimental Design

BBD was utilized to investigate the impacts of three factors in 15 runs with a fully, randomized order. A three-factor 15-run BBD was created through the software Statgraphics® Centurion XVI, Version 16.1.11 (StatPoint, Inc., USA). The upper, mid, and lower levels of each factor were defined and signified according to a preliminary study performed before employing the experimental design. The factors and their levels covered in this work are listed in Table 1. The response of dependent variables and optimized conditions could be estimated [24,25], as well as a lack of fit test was also carried out for checking the suitability of the selected model for the evaluation and representation of responses [26]. The dependent variables were the thickness of the film ($Y_1$), the initial amount of ATC diffused after 2 h ($Y_2$)), the cumulative amount of ATC diffused after 12 hrs. ($Y_3$), steady-state flux ($Y_4$), permeability coefficient ($Y_5$), and diffusion coefficient ($Y_6$). The composition of the runs and recorded responses generated by BBD are listed in Table 2.

TABLE 1

Box-Behnken design independent levels and dependent variables with the specified responses and assigned goals of ATC-loaded transdermal film formulations.

| Independent variables (Factors) | Levels | | | Units |
| --- | --- | --- | --- | --- |
| | Low | Medium | High | |
| (A) $X_1$: Eudragit RLPO Concentration | 5 | 7.5 | 10 | (%) |
| (B) $X_2$: PEG 400 Concentration | 30 | 35 | 40 | (%) |
| (C) $X_3$: Oleic acid Concentration | 10 | 15 | 20 | (%) |

| Dependent variables (Responses) | Units | Goal |
| --- | --- | --- |
| $Y_1$: Film thickness | mm | Minimize |
| $Y_2$: Initial ATC permeated after 2 h | (%) | Maximize |
| $Y_3$: Cumulative ATC permeated after 12 h | (%) | Maximize |
| $Y_4$: Steady State Flux ($J_{ss}$) | mg/cm$^2$h | Maximize |
| $Y_5$: Permeability Coefficient ($P_c$) | (cm/h) × $10^{-4}$ | Maximize |
| $Y_6$: Diffusion Coefficient (D) | (cm$^2$/h) × $10^{-3}$ | Maximize |

TABLE 2

Composition of Box-Behnken design for ATC-loaded transdermal film formulations and observed values of the studied responses.

| | Factors | | | Responses* | | | | $Y_5$ | $Y_6$ |
| --- | --- | --- | --- | --- | --- | --- | --- | --- | --- |
| Formulations | $X_1$ (%) | $X_2$ (%) | $X_3$ (%) | $Y_1$ mm | $Y_2$ (%) | $Y_3$ (%) | $Y_4$ mg/cm$^2$ h | (cm/h) ×$10^{-4}$ | (cm$^2$/h) ×$10^{-3}$ |
| F1 | 7.5 | 40 | 10 | 0.958 | 20.61 | 88.94 | 0.22 | 8.947 | 1.177 |
| F2 | 5 | 30 | 15 | 0.846 | 36.04 | 94.9 | 0.221 | 8.99 | 1.187 |
| F3 | 10 | 30 | 15 | 1.236 | 22.82 | 79.16 | 0.174 | 7.066 | 0.716 |
| F4 | 5 | 35 | 20 | 0.841 | 39.85 | 97.48 | 0.205 | 8.316 | 1.027 |
| F5 | 10 | 35 | 10 | 1.245 | 17.84 | 75.67 | 0.191 | 7.768 | 0.888 |
| F6 | 7.5 | 40 | 20 | 1.285 | 35.06 | 93.4 | 0.173 | 7.046 | 0.756 |
| F7 | 5 | 40 | 15 | 0.683 | 38.56 | 95.89 | 0.185 | 7.425 | 0.84 |
| F8 | 10 | 40 | 15 | 1.238 | 19.86 | 87.89 | 0.249 | 10.12 | 1.481 |
| F9 | 7.5 | 30 | 20 | 1.13 | 38.67 | 94.23 | 0.223 | 9.054 | 1.212 |
| F10 | 5 | 35 | 10 | 0.857 | 30.85 | 93.88 | 0.2 | 8.144 | 0.984 |
| F11 | 10 | 35 | 20 | 1.348 | 26.2 | 86.89 | 0.156 | 6.332 | 0.612 |
| F12 | 7.5 | 30 | 10 | 0.979 | 26.32 | 85.34 | 0.185 | 7.532 | 0.834 |
| F13 | 7.5 | 35 | 15 | 1.016 | 31.82 | 88.14 | 0.181 | 7.362 | 0.826 |

TABLE 2-continued

Composition of Box-Behnken design for ATC-loaded transdermal film formulations and observed values of the studied responses.

| | Factors | | | | | | | $Y_5$ | $Y_6$ |
|---|---|---|---|---|---|---|---|---|---|
| | | | | | | | | Responses* | |
| Formulations | $X_1$ (%) | $X_2$ (%) | $X_3$ (%) | $Y_1$ mm | $Y_2$ (%) | $Y_3$ (%) | $Y_4$ mg/cm² h | (cm/h) ×10⁻⁴ | (cm²/h) ×10⁻³ |
| F14 | 7.5 | 35 | 15 | 0.986 | 33.36 | 88.88 | 0.176 | 7.167 | 0.773 |
| F15 | 7.5 | 35 | 15 | 0.823 | 34.13 | 89.56 | 0.19 | 7.73 | 0.902 |

*Values of responses are the means of triplicate measurements for each response and SD values did not exceed 5% of the stated values.

Preparation of ATC-Loaded OLA-PEG-E-RLPO Transdermal Films

ATC-loaded OLA-PEG-E-RLPO transdermal films were formulated by the solvent casting method [27]. A known weight (200 mg) of ATC was dispersed into the Eudragit RLPO solution that was made via dissolving the polymer into a DCM-methanol (1:1 v/v) mixture of solvents. The signified amounts of plasticizer (PEG 400) and permeation enhancer (OLA), based on total polymer mass, were dispersed in the mixture. The final mixture was then transferred to a Teflon Petri dish with a diameter of 6.06 cm and left to dry at 40° C. for 24 hours. After that, a backing membrane has been used to cover the prepared films (CoTran™, 3M, St Paul, USA). Ultimately, these films were cut to give an area of 6.74 cm² and stored in an airtight container under ambient conditions until used for further investigations. Non-PEGylated non-OLA ATC-loaded films were also produced with the same procedure.

Characterization of the ATC-Loaded OLA-PEG-E-RLPO Transdermal Films

The prepared ATC transdermal films were inspected visually and evaluated for the weight variation, thickness, and elongation percent [28], per our previous research work [29] regarding the importance of selecting the appropriate plasticizer and permeability enhancer for maximizing the physicochemical properties of the designed transdermal films. A specified area (1.76 cm²) at different points of the film is dried at 60° C. for 4 h and weighed. The average weight of three measurements and the standard deviation (SD) values are calculated. At three different points, the thickness of the films was determined using a digital micrometer. The thickness was measured in triplicate and the mean values and SD were calculated. An elongation testing apparatus has been adopted to assess % elongation. Concisely, a strip of the film (1×4 cm) was hanged between two clamp jaws. The distance between these clamps was set at 2 cm and a constant weight was fixed to the lower part. After 2 minutes, the length change of the film was determined and the percentage of elongation was calculated via the next equation.

$$\% \text{ elongation} = \frac{[L_2 - L_1]}{L_1} \times 100 \quad (1)$$

Where $L_1$ is the initial length and L2 is the final length of the film.

Ex-Vivo Skin Permeation Study of the ATC-Loaded OLA-PEG-E-RLPO Transdermal Films The permeation studies were performed utilizing an automated Franz diffusion cell apparatus (MicroettePlus™, Hanson Research, Chatsworth, Calif., USA) with a diffusion area of 1.76 cm². A 4 cm² area of full-thickness skin obtained from the shaved abdominal region of Sprague Dawley male rats (175-200 g body weight) was removed, freed from any subcutaneous adipose tissue, and inspected carefully to assure uniform thickness and integrity of the skin. The removed skin was then positioned between the donor and the receiver compartments. The dermal side was taken into consideration to be contacted directly to the donor medium. The receiver medium was composed of phosphate buffer saline (pH 7.2) with 0.05% w/v sodium dodecyl sulfate, which was maintained at 32±0.5° C. temperature and 400 rpm stirring rate. At definite time intervals, samples were withdrawn from the receiver media and substituted with fresh media. The withdrawn samples were analyzed for ATC permeated amount through the HPLC method previously mentioned. The patterns of the permeation of ATC were created via plotting the cumulative amount of ATC permeated through constant/unit area versus time. From the slope of the yielded plots, the steady-state flux ($J_{ss}$) was calculated, while the permeability coefficient (Pa) was estimated as the ratio of the flux to the initial drug load ($C_0$). The diffusion coefficient (D) was calculated from plotting the cumulative amount of ATC permeated through constant/unit area as a function of the square root of time ($\sqrt{t}$) [29] as represented in the following equation.

$$D = \left(\frac{\text{Slope}}{2C_0}\right)^2 \times \pi \quad \text{Higuchi model} \quad (2)$$

Elaboration and Assessment of the Optimized ATC-Loaded OLA-PEG-E-RLPO Transdermal Film The different response variables were measured for the fifteen designed formulations to obtain the results needed to select the optimum formula. The desirability study and multiple response optimization were performed by the software for the prediction of the composition of the optimum formula for all response variables together, and then the optimized formula was prepared. The prepared optimized formula was evaluated where the six response variables were measured under the same procedures of the fifteen formulations prepared according to BBD to be compared with the predicted variable responses [30].

In Vivo Studies on the Poloxamer-Induced Dyslipidemic Rats

Animals and Handling Procedure

Forty-eight male Sprague Dawley rats (175-220 g body weight) were utilized in this study. Eighteen rats were used for the PK study, another eighteen rats were used for the PD evaluation, and twelve rats were specified as the normal negative and model positive control groups (six rats per group), which undergo the histologic examination. This number of rats was considered enough for blood sampling by an alternative method. In this study, a single-dose one-period parallel design was used. The study was performed following Good Clinical Practice (GCP), International Conference on Harmonization (ICH), the European Medicines Agency (EMA), and Food and Drug Administration (FDA) guidelines. The study was achieved according to the Declaration of Helsinki, the Guiding Principle in Care and Use of Animals (DHEW production NIH 80±23), and the "Standards of Laboratory Animal Care" (NIH distribution #85±23, reconsidered in 1985). The rats were kept in cages on a 12 h light/dark cycles at 25° C. and 55±10% relative humidity. Rats were maintained with free access to water and ad libitum. General and environmental conditions were strictly monitored.

The categorization of animal groups was the same in both PK and PD studies, where the animals were divided into three groups of six animals in each study (FIG. 1). Two groups were nominated as test groups, one received the optimized ATC-loaded OLA-PEG-E-RLPO transdermal film and the other received a non-PEGylated non-OLA ATC-loaded transdermal film, while the third (reference) group was administered the commercial oral ATC tablet (Lipitor® 10 mg). Dyslipidemia was induced in the animals of the PD study groups and the model group specified for the histologic examination. The dyslipidemic-induction was done via 0.25 g/kg poloxamer 407 intraperitoneal (i.p.) injection, which was previously dissolved in 0.9% saline [31]. Regarding dosage administration in PK and PD study groups, and 24 h after poloxamer 407 injection in PD study groups, the reference group was orally administered 1 ml of 0.5% carboxymethyl cellulose aqueous suspensions containing the pulverized ATC tablet (equivalent to 10 mg/kg body weight) through esophageal intubation, while the test groups were administered the optimized ATC-loaded OLA-PEG-E-RLPO transdermal film and the non-PEGylated non-OLA ATC-loaded transdermal film, respectively (10 mg/kg body weight), via the transdermal application on a 3.0 cm² area of skin. The applied films were fixed well and covered with plain adhesive films. Subsequently, after the specified 72 h for both experiments, rats of PD study groups and histologic examination groups were sacrificed and liver specimens were removed, rinsed with normal saline, and preserved in 10% neutral buffered formalin for histopathological analysis. A schematic representation of utilized procedures for the in-vivo studies was summarized in FIG. 1.

Sampling Technique

Blood samples (250 µl) were collected from the PK study groups in heparinized tubes under light ether anesthesia by a retro-orbital puncture at 0, 1, 2, 4, 8, 12, 24, 48, and 72 h. The collected blood samples were centrifuged at 3000 rpm for 5 min to separate the plasma that was collected and stored at −20° C. until performing further analysis and for quantification of ATC concentration using the HPLC method mentioned before. Regarding the PD study, normal blood samples were taken immediately before the induction of dyslipidemia, to indicate the normal levels of lipid profiles under investigation. After 24 h of dyslipidemic induction, samples at 0, 2, 8, 12, 24, 48, and 72 h time points were selected for the analysis and evaluation of lipid profiles (triglycerides; TG, total cholesterol; TC, LDL, and HDL).

Assessment of Pharmacokinetic Parameters

The pharmacokinetic parameters of the optimized ATC-loaded OLA-PEG-E-RLPO transdermal film were evaluated and compared to that of the non-PEGylated non-OLA ATC-loaded transdermal film and the commercial drug tablet. The following PK parameters were calculated and specified through the non-compartmental extravascular PK model via an excel add-in program (PKsolver). The peak plasma concentration and its time ($C_{max}$ and $T_{max}$, respectively) were quantified. Areas under the curve ($AUC_{0-t}$ and $AUC_{0-\infty}$) and other PK parameters as the mean residence time ($MRT_{0-\infty}$), area under the first moment of the curve ($AUMC_{0-\infty}$), elimination rate constant and half-life ($K_{e1}$ and $t_{1/2}$, respectively), apparent total body clearance and volume of distribution (Cl and $V_d$, respectively) were also calculated. Lastly, the relative bioavailability of the optimized ATC-loaded OLA-PEG-E-RLPO transdermal film was determined [32].

Evaluation of ATC Antidyslipidemic Activity

The antidyslipidemic activity of the optimized ATC-loaded OLA-PEG-E-RLPO transdermal film was determined versus the non-PEGylated non-OLA ATC-loaded transdermal film and the commercial drug tablet, over a 72-h period. Blood samples were collected and the serum was 5 min centrifugated at 10,000 rpm. The collected serum samples were investigated for TG, TC, LDL, and HDL utilizing in-vitro diagnostic kits of an enzymatic-colorimetric methodology (Egy Chemical for Lab Tech & BioMed Diagnostics, Egypt). Blood samples from the overnight-fasted rats (that undergone PK study) were collected immediately before dyslipidemia induction to specify the TG, TC, LDL, and HDL baseline levels. Besides, blood sampling was also performed 24 h after induction and exactly at zero time immediately before applying formulations, to indicate a model of the reached dyslipidemic levels of lipid profiles (FIG. 1). These biochemical parameters have been redetermined after administering ATC to the studied groups and comparing results with the corresponding baseline values assuming that each rat is considered as its control.

Histological Examination

Liver specimens were taken randomly from the rat of each group of the PK study after the 72-h time point. Specimens from the normal and model groups specified for this examination were also taken to represent the hepatocytic histologic picture of the normal and the dyslipidemic-induced model groups, respectively. Autopsy samples were taken from the liver and fixed using neutral buffered formalin 10%. Tap water was used for washing followed by dehydration via serial dilutions of alcohol (methyl and absolute ethyl). Specimens were cleared in xylene and fixed in paraffin at 56° C. for 24 h. Paraplast wax tissue blocks were prepared for sectioning at 4 microns thickness by a rotatory microtome. Finally, the obtained tissue sections were collected on glass slides, deparaffinized, stained by hematoxylin & eosin (H&E) stain [33,34].

Statistical Analysis

All statistical analyses were performed using GraphPad Prism, version 8.4.2 Software (San Diego, Calif., USA). Regarding the plasma concentration-time curve, two-way ANOVA followed by Tukey's multiple comparisons test was done to compare each means with the other at all time points to assess the significance between groups. The biochemical parameters were also assessed for their statistical difference using the two-way ANOVA followed by Tukey's multiple comparisons test, as well as a two-tailed unpaired t-test was used to assess the difference between the biochemical parameters of the normal and model groups. Results with P<0.05 were considered significant.

Results and Discussion
Optimization of ATC-Loaded OLA-PEG-E-RLPO Transdermal Films Data obtained from preliminary studies were used for the optimization of ATC transdermal films using the 3-factor, 3-level BBD model, which was employed to inspect, augment, and evaluate the quadratic and interaction effects of the selected factors on the responses (Table 1). The percentage concentration of matrix-forming polymer; Eudragit RLPO, was assigned in this design as $X_1$ with levels of 5, 7.5, and 10%. The levels of percentage concentrations of the plasticizer, PEG 400 ($X_2$), were 30, 35, and 40%, while 10, 15 and 20% were the levels of percentage concentrations of the penetration enhancer; OLA, which was employed as $X_3$. Different response variables were measured for all the BBD formulations and the results were presented in Table 2. Polynomial equations were generated for each response. Besides, a lack of fit test summary data was also displayed in Table 3. This data revealed that the selected model for all responses has an insignificant lack of fit (its p-value more than 0.05). The lack of fit test is premeditated to reveal the suitability of the selected model to demonstrate and represent the detected data. In the case of the p-value for lack-of-fit in the ANOVA results is more than or equal to 0.05, the model seems to be suitable for the detected data at the 95.0% confidence level [26,35].

The percentage of elongation is one of the respectable means of describing the mechanical physiognomies of the film. A film with a low percentage of elongation and tensile strength is considered a soft film. Brittle/hard film is found with low elongation and moderate tensile strength, while a film with high elongation percent and tensile strength is considered a tough/soft film [36]. The obtained data (24, 7, 12, 13.5, 14, 21, 17, 19, 10, 12, 11, 13, 18, 16 and 17% for formulations from F1 to F15, respectively) exhibited elongation percentages oscillated between 7 and 24% for F2 and F1, respectively. F1 and F2 were elaborated with 40% and 30% of PEG 400 concentration, respectively (Table 2). Thus, utilizing the right percentage of plasticizer is significant and very crucial for enhancing elasticity and minimizing the brittleness of prepared films. Also, the film thickness varied from 0.683 mm in F7 to 1.285 mm in F6 by altering the levels of factors (Table 2).

To conclude, the elaborated films were of uniform weight, good elasticity, even in thickness and their appearance was appropriately smooth without any observed visible cracks. Further interpretation regarding the quantitative estimated effects of factors on film thickness along with all other responses of BBD representing the ex vivo skin permeation parameters is detailed in the next section.

TABLE 3

Parameters of lack-of-fit tests of responses.

| Responses | Sum of Squares | Degree of Freedom | Mean Square | F-ratio | Lack of Fit p-value |
|---|---|---|---|---|---|
| Y1 | 0.0303007 | 3 | 0.0101002 | 0.94 | 0.5536 |
| Y2 | 24.4544 | 3 | 8.15148 | 5.89 | 0.1485 |
| Y3 | 9.50838 | 3 | 3.16946 | 6.28 | 0.1404 |
| Y4 | 0.00112275 | 3 | 0.00037425 | 7.44 | 0.1208 |
| Y5 | 1.86514 | 3 | 0.621713 | 7.61 | 0.1184 |
| Y6 | 0.0977277 | 3 | 0.0325759 | 7.75 | 0.1165 |

Physicochemical Characterization of ATC-Loaded OLA-PEG-E-RLPO Transdermal Films

The characterization of ATC-loaded films via measuring weight, percentage of elongation, and film thickness displayed insignificant variation between the elaborated films. The percentage of weight variation for the triplicates of each type of ATC film did not exceed 5%, which indicates acceptable weight uniformity of the elaborated transdermal films.

The Quantitative Estimation of Factors' Effects

The relevancy-oriented mathematical treatment among the selected factors and the detected responses were expressed as polynomial equations and explained for their significance by ANOVA. The estimated factors' effects along with the corresponding p-values yielded by ANOVA on all responses are represented in Table 4. The effectiveness of any factor will be considered significant in case the effect value is more than zero and its p-value is not equal to or more than 0.05. Besides, the synergistic factor effect will be labeled with a positive sign, whereas the antagonistic effect is symbolized by a negative sign.

TABLE 4

Estimated effects of factors and associated P-values for the responses of ATC-loaded transdermal film formulations.

| | | Factors | | | | | | | | |
|---|---|---|---|---|---|---|---|---|---|---|
| | | $X_1$ | $X_2$ | $X_3$ | $X^1_2$ | $X_1X_2$ | $X_1X_3$ | $X^2_2$ | $X_2X_3$ | $X^2_3$ |
| $Y_1$ | Factor effect | 0.46 | −0.0068 | 0.14125 | 0.04383 | 0.0825 | 0.0595 | 0.07433 | 0.088 | 0.21833 |
| | p-values | 0.025* | 0.9351 | 0.1943 | 0.7244 | 0.5103 | 0.6245 | 0.5627 | 0.486 | 0.1808 |
| $Y_2$ | Factor effect | −14.65 | −2.44 | 11.04 | −5.263 | −2.74 | −0.32 | −2.303 | 1.05 | −3.573 |
| | p-values | 0.0032* | 0.0992 | 0.0056* | 0.0501 | 0.1452 | 0.8111 | 0.2006 | 0.4662 | 0.1001 |
| $Y_3$ | Factor effect | −13.135 | 3.1225 | 7.0425 | −1.3975 | 3.87 | 3.81 | 2.5975 | −2.215 | 0.6375 |
| | p-values | 0.0015* | 0.0249* | 0.0050* | 0.1993 | 0.0321* | 0.0330* | 0.0723 | 0.0893 | 0.4794 |

TABLE 4-continued

Estimated effects of factors and associated P-values
for the responses of ATC-loaded transdermal film formulations.

| | | Factors | | | | | | | | |
|---|---|---|---|---|---|---|---|---|---|---|
| | | $X_1$ | $X_2$ | $X_3$ | $X^1_2$ | $X_1X_2$ | $X_1X_3$ | $X^2_2$ | $X_2X_3$ | $X^2_3$ |
| $Y_4$ | Factor effect | −0.01025 | 0.006 | −0.0098 | 0.01267 | 0.056 | −0.02 | 0.037167 | −0.0425 | −0.0013 |
| | p-values | 0.1777 | 0.3543 | 0.1914 | 0.2284 | 0.0160* | 0.1062 | 0.0373* | 0.0268* | 0.8734 |
| $Y_5$ | Factor effect | −0.3973 | 0.224 | −0.4108 | 0.47583 | 2.3095 | −0.804 | 1.48533 | −1.7115 | −0.0352 |
| | p-values | 0.1883 | 0.3833 | 0.1792 | 0.2509 | 0.0150* | 0.1066 | 0.0379* | 0.0268* | 0.9167 |
| $Y_6$ | Factor effect | −0.0853 | 0.0763 | −0.069 | 0.10533 | 0.556 | −0.1595 | 0.3393 | −0.3995 | −0.0172 |
| | p-values | 0.2041 | 0.2382 | 0.2713 | 0.259 | 0.0133* | 0.1331 | 0.0374* | 0.0253* | 0.823 |

$X_1$ is Eudragit RLPO Concentration (%),
$X_2$ is the PEG 400 Concentration (%),
$X_3$ is the Oleic acid Concentration (%),
$X_1X_2$, $X_1X_3$, $X_2X_3$ are the interaction terms between the factors,
$X^2_1$, $X^2_2$, $X^3_2$ are the quadratic terms of the factors,
$Y_1$ is the film thickness (mm),
$Y_2$ is the Initial ATC permeated after 2 h (%),
$Y_3$ is the cumulative ATC permeated after 12 h (%),
$Y_4$ is the Steady State Flux ($J_{ss}$; mg/cm$^2$ h),
$Y_5$ is the Permeability Coefficient ($P_c$; cm/h × $10^{-4}$), and
Y6 is the Diffusion Coefficient (D; cm$^2$/h × $10^{-3}$).
* Significant effect of factors on individual responses.

According to the given outcomes, $X_1$ was observed to noticeably and synergistically influence the film thickness ($Y_1$) with a 0.025 p-value. Besides, $X_1$ was also noted to significantly and antagonistically affect both percentages of the initial and cumulative ATC amount permeated after 2 h ($Y_2$), and 12 h ($Y_3$) with 0.0032 and 0.0015 p-values, respectively. The only effect showed from $X_2$ was a significant positive influence on $Y_3$ with a p-value of 0.0249. $X_3$ was also found to exhibit a positive influence on both $Y_2$ and $Y_3$ with 0.0056 and 0.005 p-values, respectively. Furthermore, $Y_3$, $Y_4$, $Y_5$, and $Y_6$ are influenced synergistically by the interaction term ($X_1X_2$), while the interaction term ($X_1X_3$) influenced positively $Y_3$ without any other significant effects on other responses. In addition, it was noted that the quadratic term of $X_2$ possessed a noticeable positive effect on $Y_4$, $Y_5$, and $Y_6$. On the other hand, a significant antagonistic effect on $Y_4$, $Y_5$, and $Y_6$ was exhibited by the interaction term ($X_2X_3$). The quadratic terms of $X_1$ and $X_3$ were found to have no significant effects on any of the measured responses (Table 4).

Estimated Effects on Film Thickness ($Y_1$)

From the data presented in Table 2, the film thickness was varied from 0.683 mm in F7 to 1.285 mm in F6. The film thickness ($Y_1$) was mainly influenced by $X_1$ with a positive trend, which is logical to observe the increase in film thickness along with the increase of the amount of polymer used for preparation. This finding was demonstrated in both the Pareto chart and the contour response surface plot of $Y_1$ (FIGS. 2 and 3). At $X_2$ and $X_3$ fixed levels in F2 and F3, the increase in $X_1$ from 5 to 10% was accompanied by a thickness increase from 0.846 to 1.236 mm. Also, the decrease of $X_1$ from 10 to 5% in F5 and F10, respectively, was found together with the decrease of the film thickness from 1.245 to 0.857 mm at constant levels of $X_2$ and $X_3$.

Estimated effects on percentages of initial and cumulative permeated ATC ($Y_2$ and $Y_3$), and ex vivo skin permeation parameters ($Y_4$, $Y_5$, and $Y_6$)

Figure 4A:
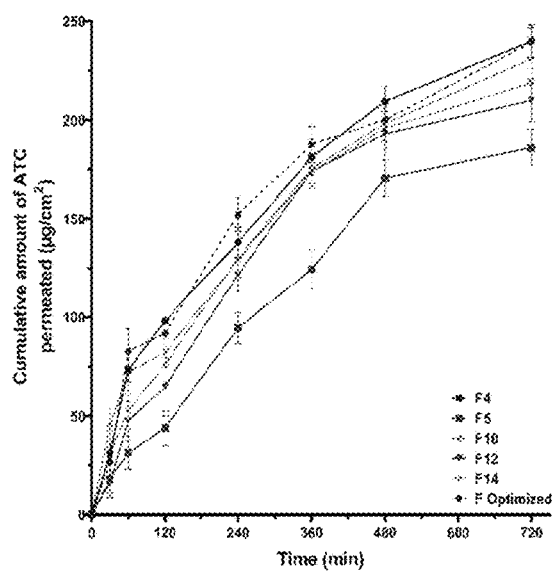
FIGS. 4A-B. Ex-vivo permeation profile of different formulations and the optimized OLA-PEG-E-RLPO transdermal film plotted in terms of the cumulative amount of ATC permeated versus time (A), and versus time square root (B).
Figure 4B:
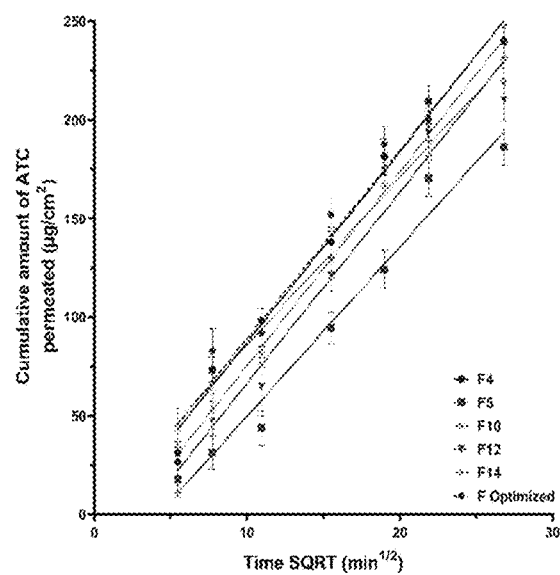
Figure 5A:
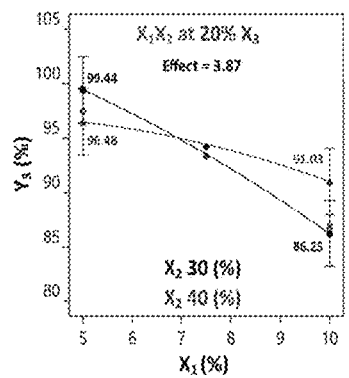
FIGS. 5A-G. Interaction plots for factors' effects on the measured cumulative amount of ATC permeated after 12 h ($Y_3$) and the measured permeability coefficient ($Y_5$). (A) $X_1$ at the low level of $X_2$ (30%), (B) interaction between $X_1$ and $X_3$ on $Y_3$ at 30% $X_2$, (C) $Y_3$ output at the low levels of $X_2$ and $X_3$, (D) $X_1$ at 30% $X_2$ and 20% $X_3$, (E) $Y_5$ output at 10% $X_3$ and 30% $X_2$, and (F) 20% $X_3$ and 5% $X_1$. (G) Schematic illustrations displaying the mechanistic intercorrelation between the factors' physicochemical physiognomies at different levels and the measured permeability outputs revealed from the plotted interactions.
Figure 5B:
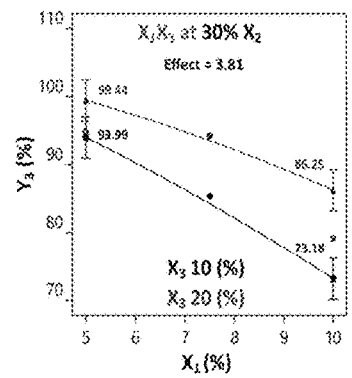
Figure 5C:
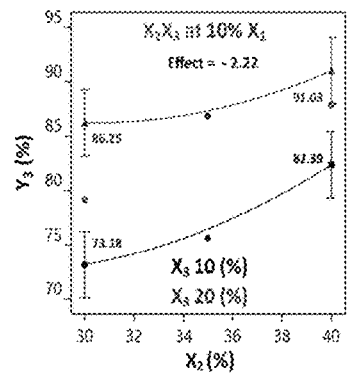
Figure 5D:
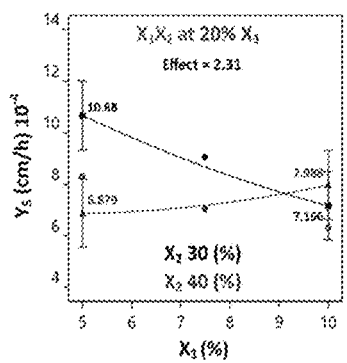
Figure 5E:
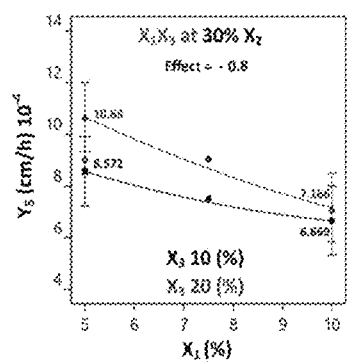
Figure 5F:
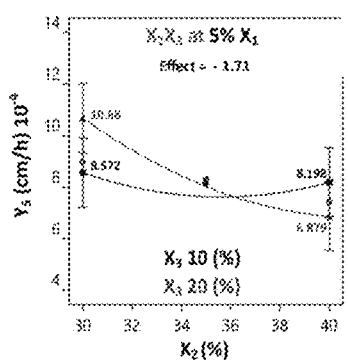
Figure 5G:
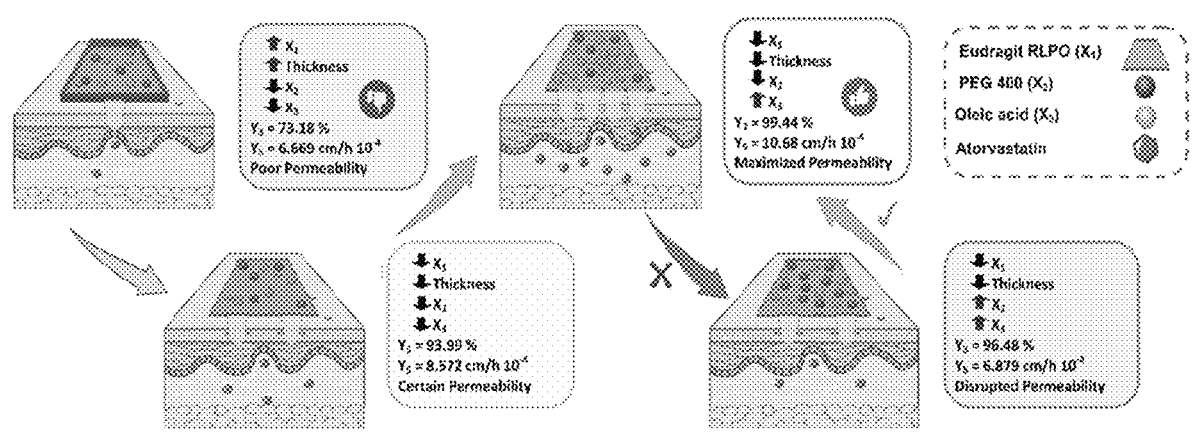
Figure 6:
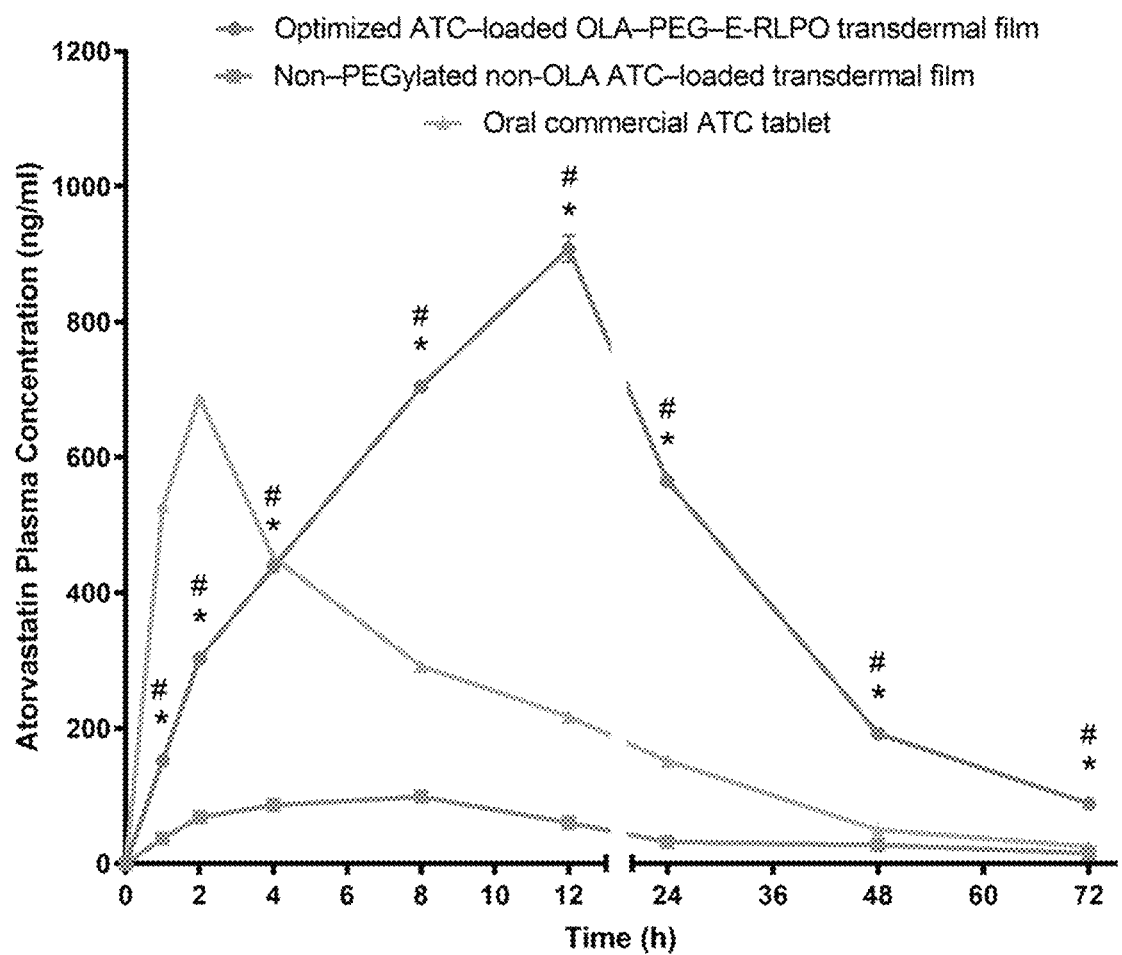
FIG. 6. Plasma concentration-time curves of atorvastatin in the optimized OLA-PEG-E-RLPO transdermal film, the non-PEGylated non-OLA ATC-loaded transdermal film, and the commercial tablets, data are presented as mean±SD, (n=6). Note: *, , and * denote significant difference of the optimized OLA-PEG-E-RLPO film versus the non-PEGylated non-OLA ATC-loaded film at P<0.05, P<0.01, and P<0.001, respectively. #, ##, and ### denote significant difference of the optimized OLA-PEG-E-RLPO film versus the oral commercial tablet at P<0.05, P<0.01, and P<0.001, respectively.

The initial permeated ATC amount was observed at 2 h while the cumulative permeated ATC amount was detected at 12 h, which were plotted in FIG. 4. Also, the other ex vivo skin permeation parameters namely; steady-state flux ($J_{ss}$; $Y_4$), permeability coefficient ($P_c$; $Y_5$), and diffusion coefficient (D; $Y_6$), were extracted from FIG. 4b and displayed in Table 2.

The percentages of initial ATC permeated after 2 h ($Y_2$) were varied from 17.84% for F5 to 39.85% for F4, while the percentages of cumulative ATC permeated after 12 h ($Y_3$) were ranged from 75.67% for F5 to 97.48% for F4. $X_1$ was the main factor inversely affecting both $Y_2$ and $Y_3$ (FIGS. 2 and 3). In F4 and F11, the increase in $X_1$ from 5 to 10% was accompanied by the decrease of the percentage of initial ATC permeated from 39.85% to 26.2%, respectively, and a decrease in cumulative permeation percentage from 97.48% to 86.89%, respectively, at the same levels of $X_2$ and $X_3$. Also, the decrease of the percentage concentration of Eudragit RLPO from 10 to 5% in F8 and F7, respectively, was accompanied by the increase of initial ATC permeated from 19.86% to 38.56%, as well as the increase of cumulative ATC permeated from 87.89% to 95.89%, respectively, at the same level of other factors. This can be explained owing to the increase in the polymer content that increases the thickness of the film, which led to the increase in the length of diffusion path traveled by ATC through the film, and thus, delay the initial and cumulative permeated drug amount [37].

Also, $X_2$ was found to positively influence the cumulative ATC permeation percentage of the formulations. This result is mainly correlated to the hydrophilicity of PEG and the enhanced wettability and can be additionally explained by the fact that low molecular weight PEGs have higher hydrophilicity than PEGs with high molecular weight, and thus it will be able to swell well and allow more drug diffusion from the films [38]. $X_3$ (OLA percentage concentration) displayed a synergistic impact on both $Y_2$ and $Y_3$. The rational positive effects of using OLA as a penetration enhancer on enhancing permeation were also confirmed in earlier studies [39,40]. Furthermore, the interaction terms ($X_1X_2$ and $X_1X_3$) also showed a synergistic influence on $Y_3$. Moreover, both $X_1X_2$ and the quadratic term of $X_2$ possessed a significant positive impact on $Y_4$, $Y_5$, and $Y_6$. In contrast, a noticeable negative influence on $Y_4$, $Y_5$, and $Y_6$ was shown by the interaction term ($X_2X_3$).

Statistical Analysis and Mathematical Modeling of the Experimental Data

After investigation of the values of all BBD studied responses, mathematical modeling for each response was yielded. Equations 3-8 describe the analysis outcomes of the multiple linear regression developed by the best-fit method.

$$\text{Film thickness } (Y_1) = 5.122 - 0.112X_1 - 0.156X_2 - 0.196X_3 + 0.004X_1^2 + 0.003X_1X_2 + 0.002X_1X_3 + 0.0015X_2^2 + 0.002X_2X_3 + 0.004X_3^2 \quad (3)$$

$$\text{Initial ATC permeated after 2 h } (Y_2) = -68.331 + 7.415X_1 + 3.488X_2 + 2.609X_3 - 0.421X_1^2 - 0.1096X_1X_2 0.013X_1X_3 - 0.046X_2^2 + 0.021X_2X_3 - 0.072X_1 \quad (4)$$

$$\text{Cumulative ATC permeated after 12 h } (Y_3) = 181.811 - 8.654X_1 - 3.821X_2 + 0.729X_3 - 0.112X_1^2 + 0.155X_1X_2 + 0.152X_1X_3 + 0.052X_2^2 - 0.044X_2X_3 + 0.013X_3^2 \quad (5)$$

$$\text{Steady—state flux } (Y_4) = 1.199 - 0.083X_1 - 0.055X_2 + 0.036X_3 + 0.001n + 0.002X_1X_2 0.001X_1X_3 + 0.0007X_1 - 0.001X_2X_3 - 0.00003X_3^2 \quad (6)$$

$$\text{Permeability coefficient } (Y_5) = 48.8823 - 3.401X_1 - 2.237X_2 + 1.419X_3 + 0.038X_1^2 + 0.092X_1X_2 0.032X_1X_3 + 0.03X_2^2 - 0.034X_2X_3 - 0.001X_{32} \quad (7)$$

$$\text{Diffusion coefficient } (Y_6) = 10.4341 - 0.826X_1 - 0.514X_2 + 0.331X_3 + 0.008X_1^2 + 0.022X_1X_2 0.0064X_1X_3 + 0.007X_{22} - 0.008X_2X_3 - 0.0003X_3^2 \quad (8)$$

Mechanistic Justification of E-RLPO, PEG 400 and OLA Intercorrelated Effects

The previous findings regarding the estimated effects of the selected polymer (E-RLPO, $X_1$), plasticizer (PEG 400, $X_2$), and permeability enhancer (OLA, $X_3$) can be mechanistically illustrated via the interaction plots between the specified factors (FIG. 5), along with many physiochemical actualities. Starting with the effect of $X_1X_2$ interaction on the cumulative permeated ATC amount at 12 h ($Y_3$) at a high level of $X_3$ (20%), it was found that the effect of $X_1$ at the high level of $X_2$ (40%) was −5.455, while the effect of $X_1$ at the low level of $X_2$ (30%) was found to be −13.195 (FIG. 5*a*). Besides, the effect of interaction between $X_1$ and $X_3$ on $Y_3$ at 30% $X_2$ (FIG. Sb) revealed that the effect of $X_1$ at 20% $X_3$ was −13.195, whereas the effect of $X_1$ at the low level of $X_3$ (10%) was −20.815. In addition, investigating the effect of interaction between $X_2$ and $X_3$ on $Y_3$ at a high level of $X_1$ (10%) revealed that the lowest ever $Y_3$ output (73.18%) was recorded at the low levels of $X_2$ and $X_3$ (FIG. 5*c*). This output was also noted in $X_1X_3$ interaction plot (FIG. 5*b*), which was also recorded at $X_1$ high level and low levels of $X_2$ and $X_3$. Regarding the effects of factors' interaction on permeability coefficient ($Y_5$), the effect of $X_1$ at 40% $X_2$ and 20% $X_3$ was found to be 1.10825, while the effect of $X_1$ at 30% $X_2$ and 20% $X_3$ was −3.51073 (FIG. 5*d*). Furthermore, the lowest $Y_5$ output ($6.669\times10^{-4}$ cm/h) was recorded at 10% $X_1$ (high level of $X_1$) and 10% $X_3$ and 30% $X_2$ (low levels of $X_2$ and $X_3$), as shown in FIG. 5*e*. These findings indicated that the increased level of $X_1$ along with the declining levels of both $X_2$ and $X_3$ had an antagonistic effect on ATC permeability and release from elaborated transdermal films. As discussed in an earlier section, an increasing amount of E-RLPO in the formulated transdermal film will yield a thicker film with a longer path for ATC to escape the film and reach the skin with a lower permeation magnitude. And vice versa, lower E-RLPO amounts will yield higher ATC release percentage and permeability magnitude (FIG. 5*g*). This rationale is further confirmed with the high $Y_3$ and $Y_5$ outputs recorded at a low level of $X_1$ (5%) in many interaction plots. For example, the highest $Y_3$ output was 99.44%, which was found to be recorded at 5% $X_1$ as shown in FIGS. 5*a* and 5*b*, while the highest $Y_5$ output was $10.68\times10^{-4}$ cm/h, which was noticed at low levels of $X_1$ as displayed in FIGS. 5*d*, 5*e*, and 5*f*.

Interestingly, the highest $Y_3$ and $Y_3$ outputs were also found at low levels of $X_2$ and high levels of $X_3$. Besides, the simultaneous existence of both $X_2$ and $X_3$ at high levels yielded an unexpected decline in the permeability of ATC through the transdermal films. In FIG. 5*f*, the permeability coefficient decreased from $10.68\times10^{-4}$ cm/h to $6.879\times10^{-4}$ cm/h with the increased level of $X_2$ from 30% to 40%, at 20% $X_3$ and 5% $X_1$. Before jumping to any conclusion, the need of designing polymeric films that retained some degree of swellability (for better diffusability) led to the selection of a low molecular weight plasticizer with high swelling and wetting ability, which in turn led to PEG 400 utilization ($X_2$) in formulating and optimizing the designed transdermal films [38]. However, using low levels of $X_2$ was found to retain a more favorable release and permeability extent than what was found at high levels of $X_2$. On the other hand, the rationale of the enhanced permeability with utilizing high levels of OLA ($X_3$) can be referred to as the ability of OLA higher concentrations in forming separate phases within the stratum corneum and thus generating permeability gates or pools with much-improved diffusion of drugs [41]. Although OLA has a good permeability enhancing capacity in both low and high water content skin conditions [42], using high levels of PEG 400, and therefore much more hydrophilicity, will potentially affect the OLA-generated permeability gates, diminish the efficiency of OLA, and thus will lead to a disrupted permeability, as illustrated in FIG. 5*g*.

To emphasize, $X_1$ levels should be kept as low as possible with the attempt to optimize PEG 400 level in presence of OLA, for elaborating transdermal films with maximized permeability and release physiognomies.

Prediction and Assessment of the Optimized ATC-Loaded OLA-PEG-E-RLPO Transdermal Film Multiple response optimization can yield an optimized ATC-loaded OLA-PEG-E-RLPO transdermal film that achieves the required goals in procuring minimal values of film thickness and maximal values of initial and cumulative permeation after 2 h and 12 h, respectively, steady-state flux, permeability coefficient, and diffusion coefficient. The optimized parameters were anticipated and investigated to compromise amongst responses to get a combination of factors' levels that intensify the desirability function over the study goals [43]. $X_1$, $X_2$, and $X_3$ optimized levels were quantified and found to be 5, 30, and 18% for Eudragit RLPO, PEG 400, and OLA percentage concentrations, respectively. The optimized ATC-loaded OLA-PEG-E-RLPO transdermal film, with the abovementioned factors' optimized levels, were prepared and assessed as previously illustrated in the earlier section (Section 2.6). The detected values were observed to be 0.79 mm, 37.34%, 97.23%, 0.172 mg/cm$^2$ h, $7.01\times10^{-4}$ cm/h, and $0.713\times10^{-3}$ cm$^2$/h, for $Y_1$, $Y_2$, $Y_3$, $Y_4$, $Y_5$, and $Y_6$, respectively, while the predicted values of these responses were 0.85 mm, 38.94%, 98.15%, 0.253 mg/cm$^2$ h, $10.2\times10^{-4}$ cm/h, and $1.48\times10^{-3}$ cm$^2$/h, respectively.

Evaluation of the Pharmacokinetic Parameters of Optimized ATC-Loaded OLA-PEG-E-RLPO Transdermal Film The plasma concentration-time profiles for the optimized ATC-loaded OLA-PEG-E-RLPO transdermal film, the non-PEGylated non-OLA ATC-loaded transdermal film and the commercial drug tablet are signified in FIG. 6. The values of the pharmacokinetic parameters for ATC from all formulations are summarized in Table 5. This data indicated that optimized transdermal film improved the relative bioavailability of ATC over the non-PEGylated non-OLA ATC-loaded transdermal film and the commercial tablet by 1038.6% and 277.29%, respectively. The value of $C_{max}$ of the optimized ATC-loaded OLA-PEG-E-RLPO transdermal film was 908.667 ng/ml at 12 h $T_{max}$ versus 98.333 at 8 h and 687 ng/ml at 2 h for the non-PEGylated non-OLA ATC-loaded transdermal film and the commercial tablet, respectively. These findings indicate a momentous improvement in the PK parameters of ATC from the optimized OLA-PEG-E-RLPO transdermal film, which also confirm the significance of the incorporation of penetration enhancer (OLA) and plasticizer (PEG 400) in the optimized OLA-PEG-E-RLPO transdermal film when compared to the non-PEGylated non-OLA transdermal film [44,45]. The two-way ANOVA showed a significant difference among the studied groups ($P<0.05$) at all of the sampling points which indicates the significant improvement achieved by the transdermal delivery of ATC. Despite the fast onset achieved by the commercial tablet, it cannot be considered as superior over the 10 h delay in T. of the optimized OLA-PEG-E-RLPO transdermal film, but in contrast, this can potentially confirm much better control for the antidyslipidemic activity of ATC over a longer period. According to the chronic nature of any dyslipidaemic disorder, the enhanced bioavailability along with the prolonged duration of efficacy will improve the convenience, adherence, and compliance for dyslipidemic patients. This improvement was furthery assessed and confirmed by the biochemical analysis of TC, TG, HDL, and LDL, along with the histopathological study findings.

eters of the model group with the normal rat group. It is worthy to note that two groups of animals that received the plain films (without ATC) of the optimized and non-PEGylated non-OLA films, respectively, were considered negative control and have been performed in a previous preliminary (pilot) study, and these groups showed no significant difference when compared with the model group.

Serum Triglycerides/Total Cholesterol Assessment

Figure 7A:
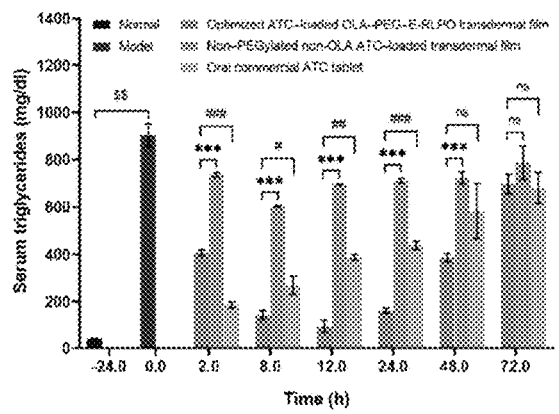
FIGS. 7A-D. Lipid profiles of dyslipidemia-induced rats after applying a single dose of each the optimized OLA-PEG-E-RLPO transdermal film, the non-PEGylated non-OLA ATC-loaded transdermal film, and the commercial tablets. Data are represented as mean±SEM, (n=3). Note: S, and SSS denote significant difference of normal versus model at P<0.05, P<0.01, and P<0.001, respectively. *, , and * denote significant difference of the optimized OLA-PEG-E-RLPO film versus the non-PEGylated non-OLA ATC-loaded film at P<0.05, P<0.01, and P<0.001, respectively. #, ##, and ### denote significant difference of the optimized OLA-PEG-E-RLPO film versus the oral commercial tablet at P<0.05, P<0.01, and P<0.001, respectively. While (ns) denotes no significant difference.

The effect of ATC on TG in dyslipidaemic rats is shown in FIG. 7a. The levels of TG in the dyslipidaemic model group were significantly higher than those in the control group ($P<0.01$), using an unpaired t-test with Welch's correction. Also, the treatment with the non-PEGylated non-OLA transdermal film showed no significance in reducing TG levels for almost all time points of the 72-h duration versus the model group. After two hours of treatment with the commercial ATC tablet and the optimized OLA-PEG-E-RLPO transdermal film, the levels of triglycerides were significantly decreased ($P<0.01$) by 79.43% and 55%, respectively, compared with the dyslipidaemic model group. Despite the significant reduction approached with the ATC oral tablets versus the model group, they only succeeded to bring TG concentration to the borderline level (185.7 mg/dl) after 2 h of administration. Furthermore, the ATC oral tablets displayed an increased gradient of hypertriglyceridemia at all other time points during the study, which failed to efficiently reduce TG levels and even reach the borderline concentrations. Interestingly, the optimized OLA-PEG-E-RLPO transdermal film significantly reduced TG levels, compared to the model group, which reached the normal levels at 8- and 12-h time points with 142.6 mg/dl (84.2% reduction) and 92.84 mg/dl (89.72% reduction) TG levels,

TABLE 5

In-vivo pharmacokinetic parameters of PEGylated with oleic acid film, non-PEGylated non-OLA film and oral commercial ATC tablet.

| Parameters (unit) | PEGylated with oleic acid film (±SD) | Non-PEGylated non-OLA film (±SD) | Oral commercial ATC tablet (±SD) |
|---|---|---|---|
| $K_{el}$ (h$^{-1}$) | 0.0395$^a$ (±0.001) | 0.0186$^b$ (±9 × 10$^{-4}$) | 0.0388 (±3.9 × 10$^{-3}$) |
| $t_{1/2}$ (h) | 17.57$^a$ (±0.469) | 37.27$^b$ (±1.819) | 18.01 (±1.782) |
| $T_{max}$ (h) | 12$^{a,b}$ | 8$^b$ | 2 |
| $C_{max}$ (ng/ml) | 908.667$^{a,b}$ (±19.76) | 98.333$^b$ (±2.517) | 687 (±9.165) |
| AUC$_{0-t}$ (ng/ml × h) | 27826.67$^{a,b}$ (±362.98) | 2679.333$^b$ (±269.03) | 10035.167 (±237.285) |
| AUC$_{0-\infty}$ (ng/ml × h) | 30067.64$^{a,b}$ (±489.36) | 3510.5$^b$ (±524.58) | 10694.91 (±427.31) |
| AUC$_{0-t/0-\infty}$ | 0.926$^a$ (±0.006) | 0.767$^b$ (±0.0392) | 0.939 (±0.01814) |
| AUMC$_{0-\infty}$ (ng/ml × h$^2$) | 875117.4$^{a,b}$ (±31022.6) | 173327.1 (±45627.8) | 247490.9 (±33619.4) |
| MRT$_{0-\infty}$ (h) | 29.1 (±0.66) | 48.8$^b$ (±5.925) | 23.1 (±2.2516) |
| $V_d$ [(mg/kg)/(ng/ml)] | 0.008$^{a,b}$ (±1.733 × 10$^{-4}$) | 0.155$^b$ (±0.0165) | 0.024 (±0.00161) |
| Cl[[(mg/kg/ng/ml)]/h | 0.0003$^{a,b}$ (±5.7 × 10$^{-4}$) | 0.003$^b$ (±4.44 × 10$^{-4}$) | 0.001 (±3.662 × 10$^{-5}$) |

$^a$Significantly different from values of non-PEGylated non oleic acid film with p-value <0.05.
$^b$Significantly different from values of oral commercial ATC tablet with p-value <0.05.

Pharmacodynamic Assessment of the Optimized ATC-Loaded Transdermal Film

The effect of both ATC-loaded films versus the ATC oral tablet on the serum TG and TC levels were evaluated in a dyslipidaemic-induced rat, in which the circulating levels of TC, TG, and LDL were elevated after poloxamer 407 injection. The induction of dyslipidemia was confirmed by the milky appearance of the blood sample withdrawn from the rats after 24 h of poloxamer injection (at zero time point) and by the significant elevation of the lipid profile paramrespectively, and approached the borderline TG level (161.6 mg/dl) at 24-h time point (FIG. 7a). These results showed that the optimized OLA-PEG-E-RLPO transdermal film was of superior efficiency over the commercial ATC tablets in normalizing the TG levels in dyslipidaemic-induced rats.

Figure 7B:
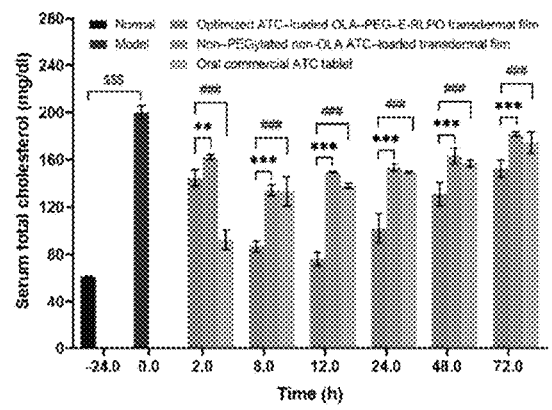

Regarding TC, all formulations showed decreased TC levels over the 72-h period (FIG. 7b). However, the optimized OLA-PEG-E-RLPO transdermal film showed the best significant TC reduction profile versus the commercial ATC tablet and the non-PEGylated non-OLA transdermal film (P<0.01). Interestingly, the optimized film showed TC reduction percentage that steadily augmented by time until 12 h time point in dyslipidemia-induced rats, with 27.8% and 62% reduction in TC levels at 2 h and 12 h time points, respectively, versus the model group. The overall findings exceeded the expectations regarding the reduction percentage of TG and TC levels [46,47], as well as the enhancement capacity of the optimized ATC-loaded OLA-PEG-E-RLPO transdermal film over the non-PEGylated non-OLA transdermal film and the conventional ATC tablets.

Serum Lipoproteins Evaluation

Figure 7C:
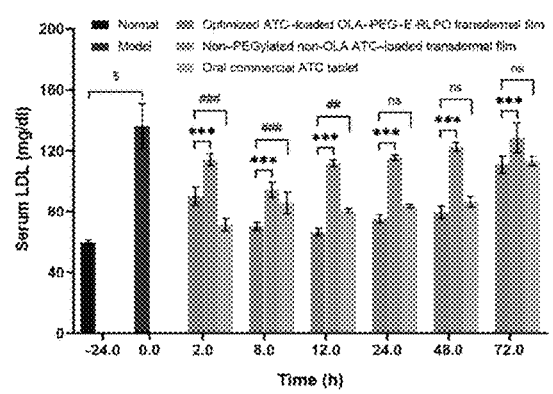

As shown in FIG. 7c, the treatment of dyslipidaemic rats with ATC, in the form of the prepared optimized ATC-loaded OLA-PEG-E-RLPO transdermal film, commercial tablets, or the non-PEGylated non-OLA transdermal film tended to decrease serum levels of LDL compared to the model group. The optimized transdermal film significantly decreased the serum LDL levels throughout the PD study versus the non-PEGylated non-OLA transdermal film (P<0.001). However, the commercial tablets made more reduction percentage in the LDL levels in serum after 2 h by 47.7% than the percent decrease in the serum LDL levels displayed by the optimized transdermal film (33.55%). On the other hand, after 8, and 12 h, the optimized transdermal film displayed a significant reduction in the serum LDL levels compared to the commercial tablets by 48.45% and 51.2%, respectively (FIG. 7c).

Figure 7D:
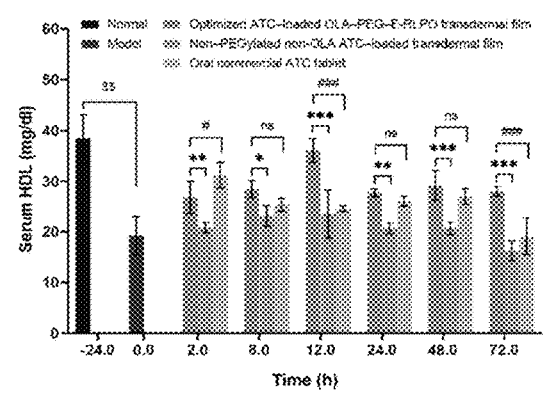

In contrast to LDL, the level of HDL was increased in the serum of dyslipidaemic rats treated with the optimized ATC-loaded OLA-PEG-E-RLPO transdermal film, commercial tablets, and the non-PEGylated non-OLA transdermal film. In particular, at a 2 h time point, the optimized transdermal film formulation raised the serum HDL by 39.75% compared to the 62.83% increase in HDL serum levels in the commercial tablets pre-treated group. While at 8 h, the serum HDL was increased by 87.85%, which is significantly different from the 28.21% increase in HDL levels made by commercial ATC tablets (P<0.001) (FIG. 7d). These results indicated that ATC could decrease the risk of coronary disease and atherosclerosis by raising the level of HDL and lowering LDL levels.

Results obtained from the pharmacokinetic and pharmacodynamic studies indicated an enhancement in ATC bioavailability and hypolipidemic activity after treatment with the optimized ATC-loaded OLA-PEG-E-RLPO transdermal film. The lipid profile of the animal group pre-treated with the optimized ATC-loaded OLA-PEG-E-RLPO transdermal film achieved the normal levels at 12 h, besides the significant enhancement over the TG, TC, LDL, and HDL levels exhibited by the pre-treated groups of both the non-PEGylated non-OLA ATC-loaded film and the oral commercial ATC tablet. This enhancement enables decreasing in both the drug dose and side effects. The pharmacological activity of ATC is also of more potency from the optimized ATC-loaded OLA-PEG-E-RLPO transdermal film containing ATC dose equivalent to the dose available in the corresponding commercial tablet.

Histopathological Evaluation of Hepatic Specimens

Figure 8A:
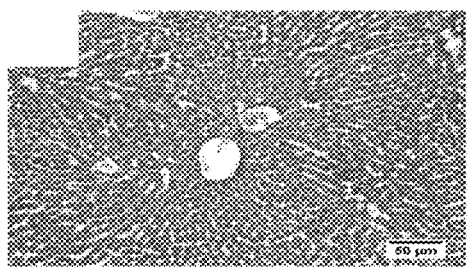
FIGS. 8A-J. Histopathological images of liver specimens stained with H&E (200×). (A, B) liver tissue from the normal group showing normal hepatocytes in which the central vein is surrounded by radiating cords of hepatocytes. (C, D) liver tissue from the model group showing portal mononuclear inflammatory cells infiltration, along with marked hepatocellular vacuolation, extensive hemorrhage, and massive hepatocellular necrosis. (E, F) liver tissue from the commercial oral ATC tablet pre-treated group, showing moderate portal mononuclear inflammatory cells infiltration with congested portal blood vessels, notice the vacuolated hepatocytes. (G, H) liver tissue from the optimized OLA-PEG-E-RLPO transdermal film pre-treated group, showing mild hepatocellular vacuolation with few necrotic hepatocytes and another image showing the normal centrilobular area (H). (I, J) liver tissue from the non-PEGylated non-OLA ATC-loaded transdermal film pre-treated group, showing a focal area of hepatocellular necrosis with intense periportal mononuclear inflammatory cells infiltration, along with fibroplasia and diffuse hepatocellular vacuolation.
Figure 8B:
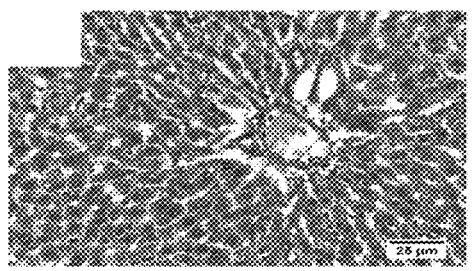
Figure 8C:
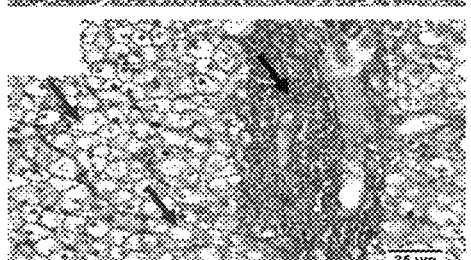

The microscopic examination of the liver from the normal group revealed normal histologic structure, and the hepatocytes are orderly arranged in normal lobular architecture with central veins and radiating hepatic cords (FIG. 8A). The portal triads showed normal histological structure containing branches of the hepatic artery, hepatic portal vein, and bile duct. On the other hand, the liver of the model group (FIG. 8B) exhibited marked diffuse hepatocellular vacuolation, in which the cytoplasm of the hepatocytes appeared pale in color with central, eccentric, or peripherally situated nuclei. The portal areas are heavily infiltrated by mononuclear inflammatory cells. Some liver sections showed massive washout necrosis of the hepatocytes along with extensive hemorrhages.

Figure 8D:
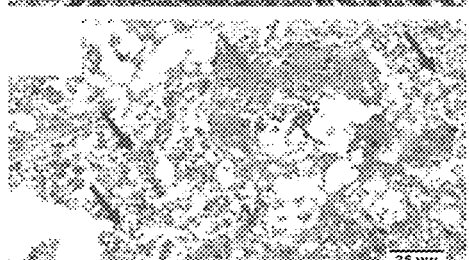
Figure 8E:
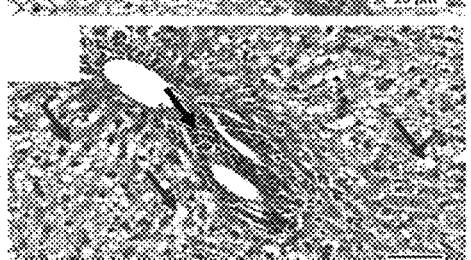
Figure 8F:
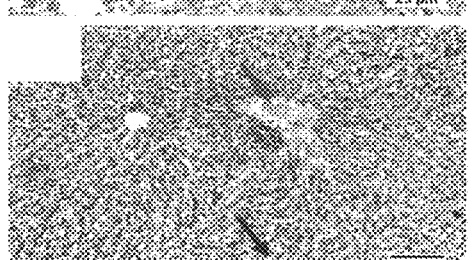
Figure 8G:
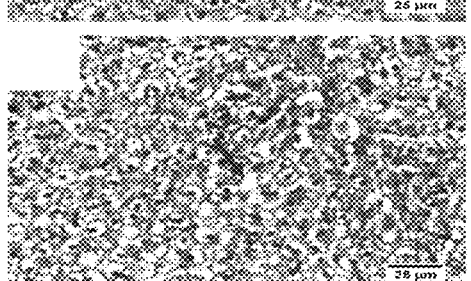
Figure 8H:
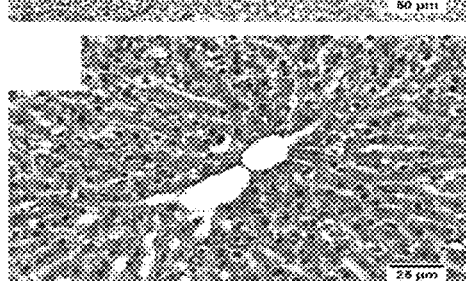
Figure 8I:
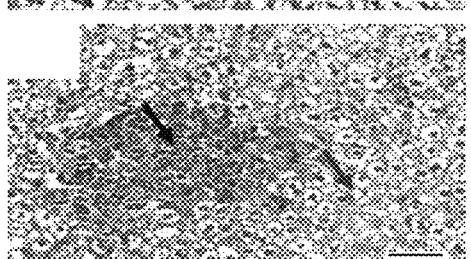
Figure 8J:
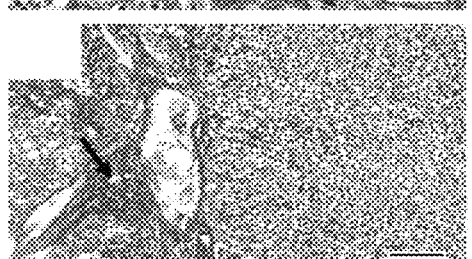

The commercial ATC tablet pre-treated group (FIG. 8C) showed only moderate improvement compared to the dyslipidemic-induced group. Vacuolation of the hepatocytes was observed with limited hepatocellular necrosis. Portal mononuclear infiltration was mild. Concerning the group that was treated with the optimized ATC-loaded OLA-PEG-E-RLPO transdermal film achieved the best hepatoprotective action; the hepatic parenchyma appeared normal in all the examined sections, and the portal areas were free from inflammatory changes (FIG. 8D). One individual exhibited mild focal hepatocellular vacuolation (FIG. 8, D1). The liver of the group treated with the non-PEGylated non-OLA transdermal film showed diffuse hepatocellular vacuolation, portal mononuclear inflammatory cells infiltration, and fibroplasia as well as focal hepatocellular necrosis in some instances (FIG. 8E).

However, the chronic use of ATC may lead to some extent of hepatological issues according to earlier studies [48,49], the optimized ATC-loaded OLA-PEG-E-RLPO transdermal film did not display noticeable histopathological changes in the hepatic tissue and is expected to minimize any hepatological side effects compared to the conventional oral tablets.

CONCLUSION

The oleic acid-reinforced PEGylated polymethacrylate (OLA-PEG-E-RLPO) transdermal films loaded with atorvastatin calcium (ATC) were designed, optimized, and elaborated. The crucial role and impact of incorporating permeability enhancer (OLA) and plasticizer (PEG 400) within the elaborated transdermal films were ex-vivolin-vivo mechanistically evaluated, which was found to exhibit exceedingly acceptable physiognomies. These films enhanced the pharmacokinetic physiognomies and exhibited noteworthy antidyslipidemic/hepatoprotective activities versus the commercial tablets as well as the non-PEGylated non-OLA transdermal film loaded with pure ATC. No noticeable hepatic histopathologic abnormalities were detected from the application of the optimized ATC-loaded transdermal film. The specified design, film components, and elaboration technique in this study have a strong opportunity for its forthgoing into the scale-up production process via utilizing an economic approach along with the mutual retaining of the enhanced efficacy. Therefore, the optimized ATC-loaded OLA-PEG-E-RLPO transdermal film can be considered as an alternative to the marketed ATC product with better adherence and dyslipidemia control.

REFERENCES

[1] M. Schachter, Chemical, pharmacokinetic and pharmacodynamic properties of statins: an update, Fundam Clin Pharmacol. 19 (2004) 117-125. doi:10.1111/j.1472-8206.2004.00299.x.

[2] F. Mctaggart, P. Jones, Effects of Statins on High-Density Lipoproteins: A Potential Contribution to Cardiovascular Benefit, Cardiovasc Drugs Ther. 22 (2008) 321-338. doi: 10.1007/s10557-008-6113-z.

[3] J. T. Davies, S. F. Delfino, C. E. Feinberg, M. F. Johnson, V. L. Nappi, J. T. Olinger, A. P. Schwab, H. I. Swanson, Current and Emerging Uses of Statins in Clinical Therapeutics: A Review, Lipid Insights. 9 (2016) 13-29. doi:10.4137/LPI.S37450.

[4] S. P. Adams, M. Tsang, J. M. Wright, Atorvastatin for lowering lipids, Cochrane Database Syst Rev. (2017) 1-24. doi:10.1002/14651858.CD008226.pub3.www.cochranelibrary.com.

[5] D. S. Shaker, R. A. H. Ishak, M. A. Elhuoni, A. M. Ghoneim, Boosting transdermal delivery of atorvastatin calcium via o/w nanoemulsifying system: Two-step optimization, ex vivo and in vivo evaluation, Int J Pharm. 578 (2020) 119073. doi:10.1016/j.ijpharm.2020.119073.

[6] C. Chojnacki, A. BloNska, J. Chojnacki, The Effects of Melatonin on Elevated Liver Enzymes during Statin Treatment, BioMed Res Int. 2017 (2017) 3204504.

[7] T. Han, D. B. Das, Potential of combined ultrasound and microneedles for enhanced transdermal drug permeation: A review, Eur J Pharm Biopharm. 89 (2015) 312-328. doi:10.1016/j.ejpb.2014.12.020.

[8] C. M. Schoellhammera, D. Blankschtein, R. Langer, Skin Permeabilization for Transdermal Drug Delivery: Recent Advances and Future Prospects, Expert Opin Drug Deliv. 11 (2014) 393-407. doi:10.1517/17425247.2014.875528.Skin.

[9] A. Z. Alkilani, M. T. C. McCrudden, R. F. Donnelly, Transdermal drug delivery: Innovative pharmaceutical developments based on disruption of the barrier properties of the stratum corneum, Pharmaceutics. 7 (2015) 438-470. doi:10.3390/pharmaceutics7040438.

[10] J. Zhu, X. Tang, Y. Jia, C. Ho, Q. Huang, Applications and delivery mechanisms of hyaluronic acid used for topical/transdermal delivery—A review, Int J Pharm. 578 (2020) 119127. doi:10.1016/j.ijpharm.2020.119127.

[11] M. M. Doherty, K. S. Pang, First-pass effect: significance of the intestine for absorption and metabolism, Drug Chem Toxicol. 20 (1997) 329-344.

[12] X. Chen, Current and future technological advances in transdermal gene delivery, Adv Drug Deliv Rev. 127 (2018) 85-105. doi:10.1016/j.addr.2017.12.014.

[13] H. Marwah, T. Garg, A. K. Goyal, G. Rath, Permeation enhancer strategies in transdermal drug delivery, Drug Deliv. 23 (2016) 564-578. doi:10.3109/10717544.2014.935532.

[14] M. Qindeel, M. H. Ullah, Fakhar-ud-Din, N. Ahmed, A. ur Rehman, Recent trends, challenges and future outlook of transdermal drug delivery systems for rheumatoid arthritis therapy, J Controlled Release. 327 (2020) 595-615. doi:10.1016/j.jconrel.2020.09.016.

[15] A. K. Umar, M. Butarbutar, S. Sriwidodo, N. Wathoni, Film-forming sprays for topical drug delivery, Drug Des Devel Ther. 14 (2020) 2909-2925. doi:10.2147/DDDT.S256666.

[16] E. Touitou, B. Godin, Y. Karl, S. Bujanover, Y. Becker, Oleic acid, a skin penetration enhancer, affects Langerhans cells and corneocytes, J Controlled Release. 80 (2002) 1-7. doi:10.1016/S0168-3659(02)00004-4.

[17] R. Gupta, B. S. Dwadasi, B. Rai, S. Mitragotri, Effect of Chemical Permeation Enhancers on Skin Permeability: In silico screening using Molecular Dynamics simulations, Sci Reports. 9 (2019) 1-11. doi:10.1038/s41598-018-37900-0.

[18] A. Ahad, A. A. Al-Saleh, N. Akhtar, A. M. Al-Mohizea, F. I. Al-Jenoobi, Transdermal delivery of antidiabetic drugs: formulation and delivery strategies, Drug Discov Today. 20 (2015) 1217-1227. doi:10.1016/j.drudis.2015.06.002.

[19] A. Naik, L. A. R. M. Pechtold, R. O. Potts, R. H. Guy, Mechanism of oleic acid-induced skin penetration enhancement in vivo in humans, J Controlled Release. 37 (1995) 299-306. doi:10.1016/0168-3659(95)00088-7.

[20] P. S. Castarieda, J. J. Escobar-Chavez, A. T. Aguado, I. M. R. Cruz, L. M. Melgoza Contreras, Design and evaluation of a transdermal patch with Atorvastatin, Farmacia. 65 (2017) 908-916.

[21] M. O. Mahmoud, H. M. Aboud, A. H. Hassan, A. A. Ali, T. P. Johnston, Transdermal delivery of atorvastatin calcium from novel nanovesicular systems using polyethylene glycol fatty acid esters: Ameliorated effect without liver toxicity in poloxamer 407-induced hyperlipidemic rats, J Controlled Release. 254 (2017) 10-22. doi:10.1016/j.jconrel.2017.03.039.

[22] M. Aqil, A. Ali, Monolithic matrix type transdermal drug delivery systems of pinacidil monohydrate: in vitro characterisation, Eur J Pharm Biopharm. 54 (2002) 161-164. doi:10.1016/50939-6411(02)00059-0.

[23] U. Seshachalam, C. B. Kothapally, HPLC analysis for simultaneous determination of atorvastatin and ezetimibe in pharmaceutical formulations, J Liq Chromatogr Relat Technol. 31 (2008) 714-721. doi:10.1080/10826070701854402.

[24] M. A. Kassem, H. S. El-Sawy, F. I. Abd-Allah, T. M. Abdelghany, K. M. El-Say, Maximizing the therapeutic efficacy of imatinib mesylate-loaded niosomes on human colon adenocarcinoma using Box-Behnken Design, J Pharm Sci. 106 (2017) 111-122. doi:10.1016/j.xphs.2016.07.007.

[25] M. S. Soliman, F. I. Abd-Allah, T. Hussain, N. M. Saeed, H. S. El-Sawy, Date seed oil loaded niosomes: development, optimization and anti-inflammatory effect evaluation on rats, Drug Dev Ind Pharm. 44 (2018) 1185-1197. doi:10.1080/03639045.2018.1438465.

[26] I. Harbi, B. Aljaeid, K. M. El-Say, A. S. Zidan, Glycosylated sertraline-loaded liposomes for brain targeting: QbD study of formulation variabilities and brain transport, AAPS PharmSciTech. 17 (2016) 1404-1420. doi:10.1208/s12249-016-0481-7.

[27] K. M. El-Say, T. A. Ahmed, S. M. Badr-Eldin, U. Fahmy, H. Aldawsari, O. A. A. Ahmed, Enhanced permeation parameters of optimized nanostructured simvastatin transdermal films: Ex Vivo and In Vivo evaluation, Pharm Dev Technol. 20 (2015) 919-926. doi:10.3109/10837450.2014.938859.

[28] T. A. Ahmed, K. M. El-Say, Transdermal film-loaded finasteride microplates to enhance drug skin permeation: Two-step optimization study, Eur J Pharm Sci. 88 (2016) 246-256. doi:10.1016/j.ejps.2016.03.015.

[29] K. M. El-Say, O. A. A. Ahmed, B. M. Aljaeid, A. S. Zidan, Matrix-type transdermal films to enhance simvastatin ex vivo skin permeability, Pharm Dev Technol. 22 (2017) 492-499. doi:10.3109/10837450.2015.1102279.

[30] A. Mujtaba, M. Ali, K. *Kohli*, Statistical optimization and characterization of pH-independent extended-release drug delivery of cefpodoxime proxetil using Box-Behnken design, Chem Eng Res Des. 92 (2014) 156-165. doi:10.1016/j.cherd.2013.05.032.

[31] K. M. El-Say, T. A. A. Ahmed, O. A. A. Ahmed, H. Elimam, Enhancing the Hypolipidemic Effect of Simvastatin in Poloxamer-Induced Hyperlipidemic Rats via Liquisolid Approach: Pharmacokinetic and Pharmacodynamic Evaluation, AAPS PharmSciTech. 21 (2020) 223. doi:10.1208/s12249-020-01754-5.

[32] K. Abo-EL-Sooud, Absolute and Relative Bioavailability, in: F. J. Hock, M. R. Gralinski (Eds.), Drug Discov

[33] T. A. Ahmed, H. Elimam, A. O. Alrifai, H. M. Nadhrah, L. Y. Masoudi, W. O. Sairafi, K. M. El-Say, Rosuvastatin lyophilized tablets loaded with flexible chitosomes for improved drug bioavailability, anti-hyperlipidemic and anti-oxidant activity, Int J Pharm. 588 (2020) 119791. doi:10.1016/j.ijpharm.2020.119791.

[34] C. Layton, J. D. Bancroft, S. K. Suvana, Chapter 4-Fixation of tissues, in: S. K. Suvarna, C. Layton, J. D. Bancroft (Eds.), Bancroft's Theory Pract Histol Tech, Eighth Edi, Elsevier, London, United Kingdom, 2019: pp. 40-63. doi:https://doi.org/10.1016/B978-0-7020-6864-5.00004-9.

[35] J. Liu, J. Wang, C. Leung, F. Gao, A multi-parameter optimization model for the evaluation of shale gas recovery enhancement, Energies. 11 (2018) 654. doi:10.3390/en11030654.

[36] S. Y. Lin, C. J. Lee, Y. Y. Lin, Drug-polymer interaction affecting the mechanical properties, adhesion strength and release kinetics of piroxicam-loaded Eudragit E films plasticized with different plasticizers, J Controlled Release. 33 (1995) 375-381. doi:10.1016/0168-3659(94)00109-8.

[37] A. Khattab, S. Shalaby, Optimized Ciclopirox-Based Eudragit RLPO Nail Lacquer: Effect of Endopeptidase Enzyme as Permeation Enhancer on Transungual Drug Delivery and Efficiency Against Onychomycosis, AAPS PharmSciTech. 19 (2018) 1048-1060. doi:10.1208/s12249-017-0917-8.

[38] L. Moradkhannejhad, M. Abdouss, N. Nikfarjam, M. H. Shahriari, V. Heidary, The effect of molecular weight and content of PEG on in vitro drug release of electrospun curcumin loaded PLA/PEG nanofibers, J Drug Deliv Sci Technol. 56 (2020) 101554. doi:10.1016/j.jddst.2020.101554.

[39] G. Mao, D. Vanwyck, X. Xiao, M. C. MacK Correa, E. Gunn, C. R. Flach, R. Mendelsohn, R. M. Walters, Oleic acid disorders stratum corneum lipids in langmuir monolayers, Langmuir. 29 (2013) 4857-4865. doi:10.1021/la4002384.

[40] Y. de las M. Zulueta Diaz, K. Menghi, M. L. Guerrero, N. Nocelli, M. L. Fanani, L-Ascorbic acid alkyl esters action on stratum corneum model membranes: An insight into the mechanism for enhanced skin permeation, Colloids Surfaces B Biointerfaces. 185 (2020) 110621. doi: 10.1016/j.colsurfb.2019.110621.

[41] A. C. Williams, B. W. Barry, Penetration enhancers, Adv Drug Deliv Rev. 56 (2004) 603-618. doi:10.1016/j.addr.2003.10.025.

[42] Q. D. Pham, S. Bjorklund, J. Engblom, D. Topgaard, E. Sparr, Chemical penetration enhancers in stratum corneum—Relation between molecular effects and barrier function, J Controlled Release. 232 (2016) 175-187. doi: 10.1016/j.jconrel.2016.04.030.

[43] B. Kapoor, R. Gupta, M. Gulati, S. K. Singh, R. Khursheed, M. Gupta, The Why, Where, Who, How, and What of the vesicular delivery systems, Adv Colloid Interface Sci. 271 (2019) 101985. doi:10.1016/j.cis.2019.07.006.

[44] C. Valenta, B. G. Auner, The use of polymers for dermal and transdermal delivery, Eur J Pharm Biopharm. 58 (2004) 279-289. doi:10.1016/j.ejpb.2004.02.017.

[45] K. Kathe, H. Kathpalia, Film forming systems for topical and transdermal drug delivery, Asian J Pharm Sci. 12 (2017) 487-497. doi:10.1016/j.ajps.2017.07.004.

[46] S. Andonova, C. Vladov, B. Kunev, I. Mitov, G. Tyuliev, J. L. G. Fierro, S. Damyanova, L. Petrov, Study of the effect of mechanical-chemical activation of Co—Mo/γ-$Al_2O_3$ and Ni—Mo/γ-A12O 3 catalysts for hydrodesulfurization, Appl Catal A Gen. 298 (2006) 94-102. doi:10.1016/j.apcata.2005.09.030.

[47] M. F. R. M. A. Shuhaili, I. N. Samsudin, J. Stanslas, S. Hasan, S C Thambiah, Effects of different types of statins on lipid profile: A perspective on asians, Int J Endocrinol Metab. 15 (2017) e43319. doi:10.5812/ijem.43319.

[48] W. K. Li, H. Li, Y. F. Lu, Y. Y. Li, Z. D. Fu, J. Liu, Atorvastatin alters the expression of genes related to bile acid metabolism and circadian clock in livers of mice, PeerJ. 5 (2017) e3348. doi:10.7717/peerj.3348.

[49] M. F. Carrascosa, J. R. Salcines-Caviedes, M. I. Lucena, R. J. Andrade, Acute liver failure following atorvastatin dose escalation: Is there a threshold dose for idiosyncratic hepatotoxicity?, J Hepatol. 62 (2015) 751-752. doi:10.1016/j.jhep.2014.11.019.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A transdermal film composition, comprising:
   a film forming polymer comprising poly(ethyl acrylate-co-methyl methacrylate-co-trimethylammonioethyl methacrylate chloride) 1:2:0.2;
   oleic acid;
   polyethylene glycol (PEG); and
   atorvastatin calcium.

2. The composition of claim 1, wherein the film forming polymer is present at a concentration of 3-10 wt %.

3. The composition of claim 1, wherein the oleic acid is present at a concentration of 10-20 wt %.

4. The composition of claim 1, wherein the PEG is PEG 400.

5. The composition of claim 4, wherein the PEG 400 is present at a concentration of 25-40 wt %.

6. The composition of claim 1, wherein the atorvastatin calcium is present in an amount of 150-250 mg.

7. The composition of claim 1, wherein the film has a thickness of 0.75-0.85 mm.

8. A method of making the composition of claim 1, comprising:
   dissolving the film forming polymer in a solvent;
   dispersing atorvastatin calcium in the film forming polymer solution;
   dispersing oleic acid and PEG in the film forming polymer solution;
   drying the solution to form a film.

9. The method of claim 8, wherein the solvent comprises a 1:1 v/v mixture of dichloromethane (DCM) and methanol.

10. The method of claim 8, further comprising attaching a backing membrane to the film.

11. A method of delivering atorvastatin to a subject in need thereof, comprising applying the transdermal film composition of claim 1 to a skin surface of the subject.

* * * * *